United States Patent
Williams et al.

(10) Patent No.: US 6,713,459 B1
(45) Date of Patent: Mar. 30, 2004

(54) METHODS FOR THE PROPHYLACTIC AND THERAPEUTIC TREATMENT OF CARDIAC TISSUE DAMAGE

(75) Inventors: David L. Williams, Johnson City, TN (US); Chuanfu Li, Johnson City, TN (US)

(73) Assignee: East Tennesee State University, Johnson City, TN (US)

( * ) Notice: Subject to any disclaimer, the term of this patent is extended or adjusted under 35 U.S.C. 154(b) by 0 days.

(21) Appl. No.: 09/560,442

(22) Filed: Apr. 28, 2000

(51) Int. Cl.$^7$ ............................................ A61K 31/716
(52) U.S. Cl. .......................................... 514/54; 514/59
(58) Field of Search ..................................... 514/54, 59

(56) References Cited

U.S. PATENT DOCUMENTS

| | | | |
|---|---|---|---|
| 4,739,046 A | 4/1988 | DiLuzio | |
| 4,761,402 A | 8/1988 | Williams | |
| 4,818,752 A | 4/1989 | Williams | |
| 4,833,131 A | 5/1989 | Williams | |
| 4,900,722 A | 2/1990 | Williams | |
| 4,975,421 A | 12/1990 | Williams | |
| 5,504,079 A | * 4/1996 | Jamas et al. | 514/54 |
| 5,532,223 A | 7/1996 | Jamas | |
| 5,783,569 A | 7/1998 | Jamas | |
| 5,849,720 A | 12/1998 | Jamas | |
| 6,242,594 B1 | * 6/2001 | Kelly | 536/123.12 |
| 6,271,199 B2 | * 8/2001 | Brand et al. | 514/2 |

OTHER PUBLICATIONS

Shibuya, H. et al "Kupffer cells generate spueroxide anions and modulate reperfusion injury in rat livers after cold preservation" Hepatology, 1997, vol 25, no 2, pp. 356–360.*

Vereschagin, E. et al "Soluble glucan protects against endotoxin shock in the rat" Shock 1998, vol 9, no 3, pp. 193–198.*

Lahnborg, G. "Glucan–induced enhancement of host resistance in experimental intraabdominal sepsis" Eur. Surg. Res. 1982, vol 14, pp. 401–408.*

Browder, W. et al "Beneficial effect of enhanced macrophage function in the trauma patient" Ann. Surg. 1990, vol211, no 5, pp. 605–612.*

Kiho, Tadashi, "Anti–Inflammatory Effect of the Polysaccharide from the Fruit Bodies of Auricularia Species," *Carbohydrate Res.* 142 (1985) 344–351 (Elsevier, Amsterdam, Netherlands).

Li, Chuanfu, "Early Activation of Transcription Factor NF–kB During Ischemia in Perfused Rat Heart," *Am. J. Physiol* 276 (*Heart Cir. Physiol*, 45), H543 H552 (1999) (American Physiological Society).

Battle, James, "Ligand Binding to the (1–>3)–B–D–Glucan Receptor Stimulates NFkB Activation, but Not Apoptosis in U937 Cells," *Biochem. Biophys. Res. Commun.* 249 (1998) 499–504 (Academic Press).

Williams, David L., "Inhibiting Early Activation of Tissue Nuclear Factor–kB and Nuclear Factor Interleukin 6 with (1–>3)–B–D–glucan Increases Long–Term Survival in Polymicrobial Sepsis," *Surgery* 126 (1999) 54–65 (Mosby, Inc.).

Adams, David S., "PGG–Glucan Activates NF–kB–like and Nf–IL–6–like Transcription Factor Complexes in a Murine Monocytic Cell Line," *J. Leukocyte Biol.* 62 (1997) 865–873.

Williams, David L., "A Method for the Solubilization of a (1–>3)–B–D–glucan Isolated from *Saccharomyces cerevisiae*," *Carbohyd. Res.* v.219 (1991) 203–213 (Elsevier, Amsterdam, Netherlands).

Masihi, K. Noel, "Down–Regulation of Tumor Necrosis Factor–a, Moderate Reduction of Interleukin–1B, But Not Interleukin–6 or Interleukin 10, by Glucan Immunomodulators Curdlan Sulfate and Lentinan," *Int. J. Immunopharmac.* 29 (1997) 463–468 (Elsevier, Pergamon Press, Great Britain).

Hara, Chihiro, "Anti–Inflammatory Activity and Conformational Behavior of a Branched (1–>3)–B–D–glucan from an Alkaline Extract of *Dictyophora indusiata* FISCH," *Carbohyd. Res.* 110 (1982) 77–87 Elsevier, Amsterdam, Netherlands).

Hoffman, Orleen A., "Fungal B–glucans Modulate Macrophage Release of Tumor Necrosis Factor–a in Response to Bacterial Lipopoly–saccharide," *Immunology Letters* 37 (1993) 19–25 (Elsevier).

Ukai, Sigbo, "Polysaccharides in Fungi. XIV. Anti–Inflammatory Effect of the Polysaccharides From the Fruit Bodies of Several Fungi," *J. Pharm. Dyn.* 6 (1983) 983–990 (Pharmaceutical Society of Japan).

Li, Chuanfu, "Adenosine Prevents Activation of Transcription Factor NF–kB and Enhances Activator Protein–1 Binding Activity in Ischemic Rat Heart," *Surgery* 126 (1999) ____(Mosby, Inc., USA).

* cited by examiner

*Primary Examiner*—James O. Wilson
*Assistant Examiner*—Leigh C. Maier
(74) *Attorney, Agent, or Firm*—Susan F. Johnston

(57) ABSTRACT

The invention provides a method for treating tissue damage caused by ischemia/reperfusion, microbial infection, or sepsis using (1→3)-β-D-glucans to modulate immune response mediators and their effects.

26 Claims, 18 Drawing Sheets

METHODS FOR THE PROPHYLACTIC AND THERAPEUTIC TREATMENT OF CARDIAC TISSUE DAMAGE

STATEMENT AS TO RIGHTS TO INVENTIONS MADE UNDER FEDERALLY SPONSORED RESEARCH AND DEVELOPMENT

Portions of the present invention were made with support of the United States Government via a grant from the National Institutes of Health to David L. Williams under grant number 1 RO1 GM 53522. The U.S. Government may therefore have certain rights in the invention.

FIELD OF THE INVENTION

The present invention relates to methods for preventing and treating tissue injury. More specifically, the invention relates to methods for treating major organ (especially cardiac) tissue damage, particularly when associated with ischemia/reperfusion injury, sepsis, or microbial infection.

DESCRIPTION OF RELATED ART

Worldwide, the World Health Organization estimates that by 2020 up to 40 percent of all deaths will be related to cardiovascular disease. In 1995, cardiovascular disease accounted for almost 15 million deaths. Since 1900, cardiovascular disease has been the number one killer in the United States in every year except 1918 (the year of the influenza pandemic), and medical costs directly related to heart disease are estimated at 30 billion dollars annually. The American Heart Association estimates that approximately 59.7 million Americans have one or more types of cardiovascular disease. Ischemic heart disease and related cardiac myopathies are the major causes of cardiac dysfunction, with ischemic heart disease causing approximately 90% of cardiac mortalities. Myocyte loss, presumably due to apoptosis, is a feature of every known type of cardiomyopathy.

Treatments for ischemic disease include aspirin, adrenoceptor blocking agents, nitrates, and angiotensin converting enzyme (ACE) inhibitors. Heparin has been administered (either intravenously or subcutaneously) in conjunction with a nonspecific fibrinolytic agent such as streptokinase, anisoylated plasminogen streptokinase activator complex (APSAC), or urokinase.

Beta-adrenergic blockers and calcium channel blockers have been shown to have some beneficial effect in the treatment of patients with chronic heart failure, which often follows ischemic cardiac tissue damage. Combinations of thrombolytic therapy and beta-adrenergic blockers, nitroglycerin, heart-rate decreasing calcium antagonists, or angiotension-converting enzyme inhibitors are currently recommended to treat patients with acute myocardial infarction. Combinations of compounds administered for the purpose of constricting arteries, increasing arterial blood pressure, and dilating veins to enhance arterial blood flow to the brain and heart, have been proposed for the treatment of patients experiencing cardiac arrest (U.S. Pat. No. 5,588,422, issued to Lurie and Gold, Dec. 31, 1996). A combination of vasopressin and an adrenergic agent, for administration to a patient suffering from cardiac arrest, has also been shown to have some benefit (U.S. Pat. No. 5,827,893, issued to Lurie and Lindner, Oct. 27, 1998).

Haikala et al. (U.S. Pat. No. 5,968,959, Oct. 19, 1999) describe use of a phospholamban inhibitor to relieve the inhibitory effect of phospholamban on cardiac sarcoplasmic reticulum $Ca^{2+}$-ATPase. Araneo et al. (U.S. Pat. No. 5,977,095, Nov. 2, 1999) describe administration of a dehydroepiandrosterone (DHEA) derivative to prevent or reduce the effects of ischemia. Singh et al. (U.S. Pat. No. 5,912,019, Jun. 15, 1999) described methods of using NO donors, inhibitors of iNOS induction, and endopeptidase inhibitors to reduce ischemia/reperfusion injury. Tomaru et al. (U.S. Pat. No. 5,869,044, Feb. 9, 1999) describe the use of batroxobin (a thrombin-like enzyme derived from snake venom) to prevent or treat ischemia/reperfusion injury. Young et al. (U.S. Pat. No. 5,863,789, Jan. 26, 1999) describe the use of IL-Ira beta polypeptides and polynucleotides for treatment of cardiac ischemia. Neely (U.S. Pat. No. 6,001,842, Dec. 14, 1999) describe methods for preventing or treating ischemia/reperfusion injury in an organ by administration of a composition containing a selective $A_1$ adenosine receptor antagonist, a $P_{2x}$ purinoceptor antagonist, or both.

A variety of compounds derived from red wine or grape seed have also been demonstrated to reduce ischemia/reperfusion injury (Sato, M. et al. *J. Mol. Cell. Cardiol.* (1999) 31(6): 1289–1297).

Despite these many and varied methods of treatment, however, significant cardiac tissue damage occurs as a result of ischemia followed by reperfusion, placing the health of thousands of individuals at risk each year. Thus, there is clearly a need for more effective agents to prevent and treat cardiac tissue injury, especially cardiac tissue injury resulting from ischemia/reperfusion.

BRIEF SUMMARY OF THE INVENTION

The present invention provides a method for reducing cardiac tissue damage in a mammalian subject, particularly a human subject, comprising administering to the subject a therapeutic dosage of a (1–3)-β-D-glucan. In the method of the present invention, the therapeutic dosage is administered prior to onset of ischemia, prior to onset of symptoms of viral or bacterial infection, subsequent to onset of ischemia, or subsequent to onset of symptoms of viral or bacterial infection, particularly septicemia. The method is particularly useful for bacterial infection associated with septic sequelae. The method of the present invention is also useful for preventing or treating cardiac tissue damage resulting from infection with a virus, such as human immunodeficiency virus (HIV) or human adenovirus (Ad).

In the method of the present invention, the therapeutic dosage can be administered by standard means, including orally, parenterally, intraperitoneally, and intravenously.

The invention also provides a method for treating ischemia/reperfusion injury in a body organ of a mammalian subject, comprising administering to the subject a therapeutic dosage of a (1–3)-β-D-glucan. The organ may be a heart, lung, liver, or other major organ. The ischemia/reperfusion injury may result from, for example, myocardial infarction, pulmonary embolism, or traumatic injury resulting in blood loss.

In one embodiment, the invention provides an emergency care or other kit for treating ischemia/reperfusion injury in a mammalian subject, comprising a therapeutic dosage of a (1–3)-β-D-glucan and a pharmaceutically acceptable carrier. The therapeutic dosage can be packaged as single dosage units or bulk packaged, and the pharmaceutically acceptable carrier can be chosen from among a tablet, caplet, capsule, intravenous fluid, or other carrier.

BRIEF DESCRIPTION OF THE DRAWINGS

FIG. 12b illustrates integrated intensity, expressed as means±SEM of 5 hearts for each time point. Normal group is designated N, sham group as S, and non-specific binding is indicated as NS. P<0.05 as compared to normal (N).

DETAILED DESCRIPTION OF THE INVENTION

Figure 1:
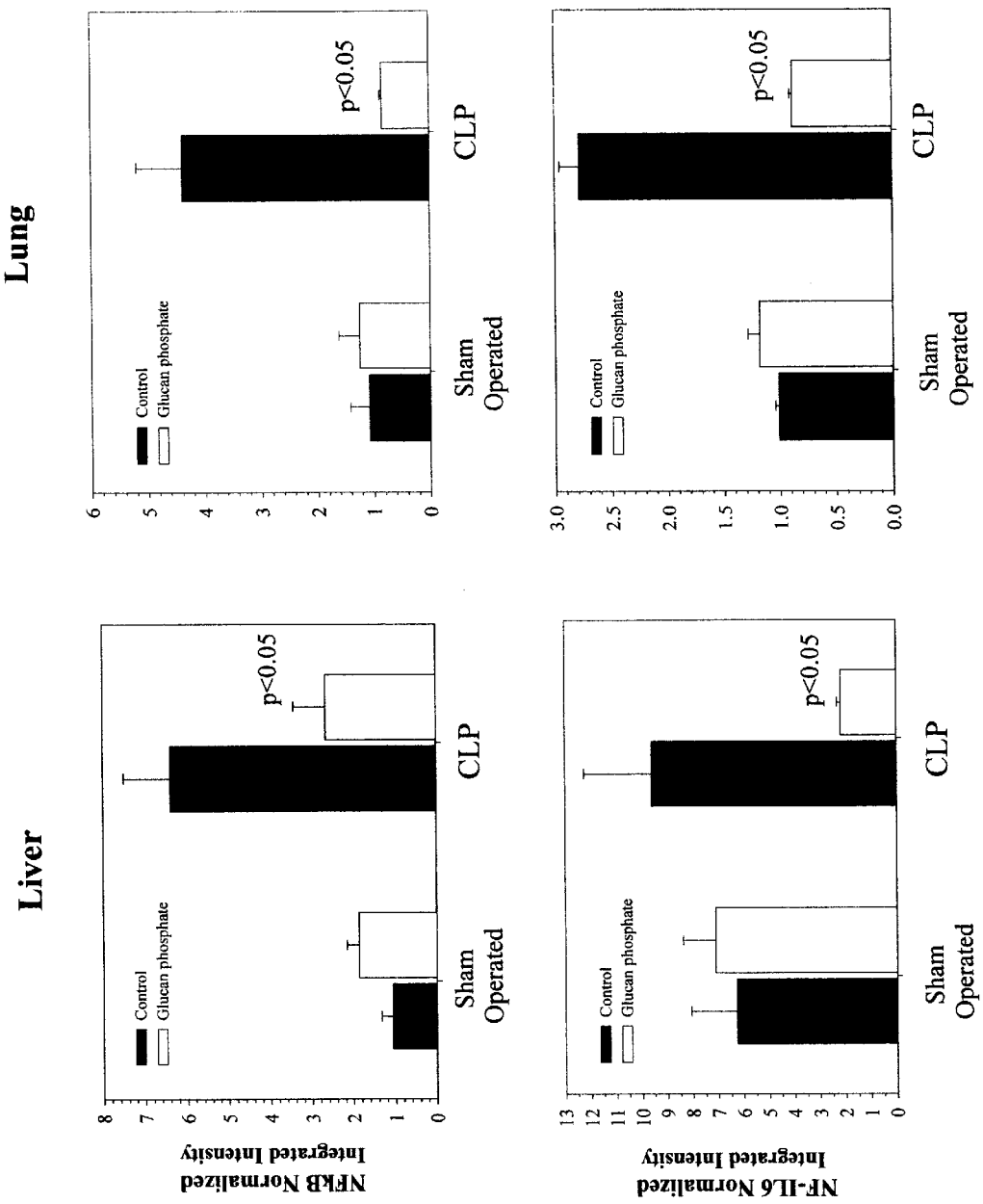
FIG. 1 illustrates results of scanning densitometry of autoradiograms derived from gel shift assays. Tissue samples were harvested 3 hours subsequent to cecal ligation and puncture (CLP) performed in ICR/HSD (Harlan Sprague-Dawley, Indianapolis, Ind.) mice, with n=4 per group. NF-κKB and NF-IL6 nuclear binding activity in liver and lung tissue were decreased in mice pretreated with glucan phosphate (50 mg/kg, injected intraperitoneally). Results are shown as normalized integrated intensity for binding activity in liver and lung tissue taken from mice subjected to CLP and to laparotomy only (LO).

The present invention provides a method of using (1→3)-β-D-glucans to significantly reduce myocardial infarct size, decrease I/R induced NFκB activation and inflammatory cytokine gene expression, and prevent cellular apoptosis, especially in the myocardium. The invention has application for treating tissue damage induced by ischemia/reperfusion, sepsis, or viral infection. The invention is especially useful for treating cardiac tissue damage prior to or following onset of ischemia/reperfusion. This method has therapeutic value for prevention of cardiac muscle damage in individuals who experience angina or who have been determined to have other risk factors for cardiac damage. Such individuals include those with HIV infection, adenovirus infection, atherosclerosis, left ventricular dysfunction (LVD), and other risk factors that have been associated with ischemia or congestive heart failure. In the method of the present invention, administration of (1–3)-β-D-glucan either prior to or subsequent to onset of ischemia, or subsequent to infection, reduces infarct size, nuclear NF-κB binding activity, TNFα mRNA levels, and cardiac myocyte apoptosis. (1→3)-β-D-glucans significantly reduced I/R mediated myocardial injury and apoptosis, providing a novel and clinically relevant management strategy for myocardial I/R injury as well as chronic heart failure.

This method is also useful for the treatment of I/R injury in other tissues, such as those of the lung, liver and kidney. Administration of two glucan preparations, each with different primary structures, molecular weight, polymer charge, polydispersity and branching frequency, demonstrated that glucans protect myocardium from I/R injury and define mechanisms of myocardial I/R injury which are common to other organs, such as liver, kidney, brain, and lung. Glucan treatment: 1) decreased I/R-induced NF-κB activation; 2) inhibited I/R stimulation of TNFα mRNA expression; 3) markedly reduced cardiac myocyte apoptosis after I/R injury; and 4) reduced myocardial ischemic infarct size.

NF-κB is present in virtually every cell type, but is retained in the cytoplasm in an inactive form bound to IκB. Upon activation of the IκB kinase (IKK) by a stimulus such as TNF-α, IL-1, LPS, etc., IκKα is phosphorylated. Once phosphorylated, IκBα is recognized by a specific ubiquitin-protein ligase, and targeted for polyubiquitinylation and degradation by the 26S proteasome. IκBα degradation exposes the NF-κB nuclear localization sequence, and NF-κB is thereby translocated to the nucleus, where it acts as a transcription factor for a variety of cellular genes, especially those involved in the inflammatory response. NF-κB regulates interferon gene expression during the antiviral response, mediates cell survival signals, and modulates cellular apoptosis. NF-κB regulation has been associated with a variety of human disorders, including neurodegenerative disease, cancers, arthritis, asthma, and a number of other inflammatory conditions. TNF-α induces degradation of IκB, thereby activating NF-κB as a transcription factor and inducing transcription of TNF-α.

Glucans are polymers of glucose that are derived from yeast, bacteria, fungi, and plants. Glucans having a β-(1–3)-linked glucopyranose backbone have been previously shown to activate the immune system, and it had previously been thought that, since soluble glucans enhance both the specific and non-specific immune response mechanisms, most soluble glucans would actually stimulate TNFα production. (See Jamas, et al., U.S. Pat. No. 5,783,569, Jul. 21, 1998). One of the present inventors had demonstrated the usefulness of soluble phosphorylated glucans generally for stimulating macrophage cells to produce cytotoxic and cytostatic factors against cancer cells, as well as for therapeutic and prophylactic antimicrobial applications (Williams, et al., U.S. Pat. No. 4,761,402, Aug. 2, 1988).

The therapeutic effects of (1→3)-β-D-glucan have been investigated in relation to septic sequelae, but little has been known about the mechanisms by which glucans exert their puzzling effects. For example, the inventors and others have reported that various glucans will stimulate NF-κB, NF-IL6, proinflammatory, and immunoregulatory cytokine production. (Battle J et al., Biochem. Biophys. Res. Commun. (1998) 249: 499–504; Adams D S, et al., J. Leukocyte Biol. (1997) 62: 865–873). In contrast, Hara et al. (Carbohyd. Res. (1982) 110: 77–87), Hoffman et al. (Immunol. Lett. (1993) 37: 19–25), Kiho et al. (Carbohyd. Res. (1988) 142: 344–351), Masihi et al. (Int. J. Immunopharmacol. (1997) 19: 463–468) and Ukai et al. (Pharmacobio Dynamics (1983) 6: 983–990) have also reported that certain glucans exert anti-inflammatory responses. Virtually nothing has been reported about the effects of glucans on myocardial I/R injury.

In the normal host, glucan binding to the (1→3)-β-D-glucan receptor stimulates a mild inflammatory and nonspecific immunostimulatory event. (Pretus H A et al., *Carbohyd. Res.* (1991) 219: 203–13; Battle J. et al., *Biochem. Biophys. Res. Commun.* (1998) 249: 499–504; Adams D. S. et al., *J. Leukocyte Biol.* (1997) 62: 865–873). Glucans would therefore appear to be contraindicated for systemic inflammatory response syndrome or sepsis. However, the inventors observed that pre- or post-treatment of septic mice with (1→3)-β-D-glucan decreased tissue NF-κB and NF-IL6 activity as well as TNF-α and IL-6 gene expression with a correlative increase in long-term survival.

Overproduction of pro-inflammatory cytokines such as TNFα, which plays a role in cardiomyocyte apoptosis, has been suggested as a mechanism for myocardial ischemia/reperfusion (I/R) injury pathogenesis and heart failure (Cain, B. S., el al. *Crit. Care Med.* (1999) 27: 1309–18), although ischemia/reperfusion injury has also been suggested to be caused by a rise in energy metabolism or an increase in active oxygen species by rapid re-oxygenation and the production of peroxide.

Although the pathologies associated with sepsis and ischemia/reperfusion injury share similarities, it has been difficult to determine whether those similarities extend to the cellular mechanisms by which tissue injury occurs. For example, although endotoxin is involved in sepsis and is known to elicit an immune response involving the same proinflammatory cytokines that had been suggested to produce cardiac tissue damage in I/R injury, administration of a bolus of endotoxin has actually been shown to protect the heart from I/R damage. Although sepsis generally causes decreased myocardial performance and increased immune response, induction of sepsis by administration of gram negative bacteria into the mouse dorsal subcutaneous space can give protection from I/R injury one hour after onset of I/R. (McDonough, K. H. et al., *Alcohol Clin. Exp. Res.* (1994) 18: 1423–1429; McDonough, K. H. et al., *Shock* (1994) 1: 432–437.) Thus, there remained significant questions regarding the role of immunomodulation in therapy for pathologies associated with significant tissue damage, particularly cardiac tissue damage. The present invention describes an important mechanism for reducing I/R-induced damage, and demonstrates a novel immunomodulatory role for (1–3)-β-D-glucans in therapy for cardiac tissue damage.

Soluble phosphorylated glucans for use in the method of the present invention, and methods for their preparation, are described in U. S. Pat. No. 4,739,046 (DiLuzio, Apr. 19, 1988), U.S. Pat. No. 4,761,402 (Williams et al., Aug. 2, 1988), U.S. Pat. No. 4,818,752 (Williams et al., Apr. 4, 1989), U.S. Pat. No. 4,833,131 (Williams et al., May 23, 1989), U.S. Pat. No. 4,900,722 (Williams et al., Feb. 13, 1990), and U. S. Pat. No. 4,975,421 (Williams, et al., Dec. 4, 1990), each of which is incorporated herein by reference.

In the method of the present invention, (1→3)-β-D-glucans are administered systemically, for example, by oral means, in combination with a pharmaceutically acceptable vehicle such as an inert diluent or an edible carrier. The glucan preparation can be composed of a single type of glucan, such as, for example, glucan phosphate, or can be composed of a mixture of two or more glucans, chosen from among the group consisting of glucan sulphate, scleroglucan, laminarin, carboxymethylated glucan, curdulan, particulate glucan, colloidal glucan, barley glucan or oat glucan. Glucans may be enclosed in hard or soft shell gelatin capsules, compressed into tablets, or incorporated directly into a patient's diet by mixing with food or appropriate liquid, such as milk or juice. For oral administration, therapeutic dosages of (1→3)-β-D-glucans may be combined with one or more excipients for use in the form of ingestible tablets, troches, capsules, caplets, wafers, buccal tablets, elixirs, suspensions, syrups, and the like. The percentage of the compositions and preparations may, of course, be varied, providing an amount of active compound within the therapeutically useful compositions such that an effective dosage level of about 1 to 150 mg/kg of patient body weight, and more preferably about 25 mg/kg to about 125 mg/kg, be administered systemically (by intravenous, intraperitoneal, subcutaneous, intradermal, or intramuscular means, for example) or up to about 1 g/kg of the patient's body weight when given orally.

Pharmaceutically acceptable vehicles, such as, for example, tablets, pills, capsules, caplets, and the like may also contain, for example, binders such as gum tragacanth, corn starch, acacia, or gelatin; excipients such as dicalcium phosphate; a disintegrating agent such as corn starch, potato starch, or alginic acid; a lubricant such as magnesium stearate, and a sweetening agent such as sucrose, fructose, lactose or aspartame. Flavoring agents, such as, for example, fruit flavoring (cherry, orange, grape and the like), peppermint, oil of wintergreen, or other flavorings known to those of skill in the art, may also be provided as a component of the pharmaceutically acceptable vehicle for administration of (1→3)-β-D-glucans in the method of the present invention. When the unit dosage form is a capsule, it may also contain a liquid carrier, such as, for example, polyethylene glycol or a vegetable oil. Solid unit dosage forms may also contain various other materials, present as coatings. For example, capsules, caplets, or tablets may be coated with sugar, gelatin, wax, or shellac. For liquid formulations, a syrup or elixir, for example, may contain one or more (1→3)-β-D-glucans in combination with a sweetening agent such as sucrose or fructose, a preservative such as propylparaben or methylparaben, and colorings or flavorings known to those of skill in the art of pharmaceutical preparation. It is understood that any material used in preparing any bulk or unit dosage form will be pharmaceutically acceptable and substantially non-toxic when administered in the amounts provided to a mammalian, particularly a human, subject. (1→3)-β-D-glucans for use in the method of the present invention may also be provided in the form of sustained-release preparations and devices, such as microcapsules. A sustained release delivery system such as, for example, that described in U.S. Pat. No. 6,007,843 (Drizen et al., Dec. 28, 1999) may be used to provide sustained release of (1→3)-β-D-glucans for use in the method of the present invention, as can the implantable controlled release device of Ashton et al. (U.S. Pat. No. 6,001,386, Dec. 14, 1999), both incorporated herein by reference.

In a preferred method of administration, (1→3)-β-D-glucans for use in the method of the present invention are administered intravenously or intraperitoneally by infusion, or injection. Pharmaceutical dosage forms suitable for injection or infusion may include sterile aqueous solutions or dispersions, for example, or sterile powders comprising (1→3)-β-D-glucans adapted for preparation of sterile injectable or infusible solutions or dispersions. Solutions containing (1→3)-β-D-glucans can be prepared in water, preferably containing isotonic agents such as sugars or appropriate salts, such as sodium chloride, optionally admixed with a nontoxic surfactant. Dispersions of (1→3)-β-D-glucans for administration in the method of the present invention can also be prepared, for example, in glycerol, triacetin, liquid polyethylene glycols, oils, or mixtures thereof. Intravenous or intraperitoneal solutions or dispersions are also provided with a preservative formulated to prevent the growth of microorganisms within the intravenous or intraperitoneal solution or dispersion.

Sterile preparations may include (1→3)-β-D-glucans encapsulated within liposomes. In any dosage form chosen for administration, the final dosage form must be sterile, fluid, and stable under standard conditions of manufacture and storage. The liquid carrier or vehicle can comprise, for example, water, ethanol, a polyol (glycerol, propylene glycol, liquid polyethylene glycols, for example) vegetable oils, nontoxic glyceryl esters, and suitable mixtures thereof. Preferably, such liquid carriers or vehicles will include isotonic agents, such as, for example, sugars, buffers or sodium chloride. Aluminum monostearate or gelatin, for example, may be incorporated with the liquid carrier or vehicle in order to prolong absorption of the injectable composition, particularly the (1→3)-β-D-glucans.

A preferred method for preparing sterile injectable solutions is combination of the (1→3)-β-D-glucans in the required amounts with various of the other ingredients described above, as required for the desired formulation, followed by filter sterilization. Vacuum drying or freeze drying techniques can be used to prepare sterile powders for the preparation of injectable solutions.

(1-3)-β-D-Glucan Therapy for Ischemia/Reperfusion Injury

The method of the present invention provides a therapy for ischemia/reperfusion injury, especially in cardiac muscle tissue. Injury can be ameliorated by administering to a patient a dosage of from about 1 mg/kg body weight to about 150 mg/kg body weight of a (1–3)-β-D-glucan such as those described in U.S. Pat. No. 4,739,046 (DiLuzio, Apr. 19, 1988), U.S. Pat. No. 4,761,402 (Williams et al., Aug. 2, 1988), U.S. Pat. No. 4,818,752 (Williams et al., Apr. 4, 1989), U.S. Pat. No. 4,833,131 (Williams et al., May 23, 1989), U.S. Pat. No. 4,900,722 (Williams et al., Feb. 13, 1990), and U.S. Pat. No. 4,975,421 (Williams, et al., Dec. 4, 1990). Glucans are effective for decreasing tissue injury when administered either prior to onset of ischemia or subsequent to onset of ischemia. Onset of ischemia can be determined by those of skill in the medical arts, by observation of symptoms associated with ischemia, such as chest pain, pressure-like discomfort, radiation of discomfort and an abnormal electrocardiogram. Less typical symptoms include diaphoresis, palpitations, nausea, dyspnea and syncope. Glucans can be administered using any of the methods and compositions previously described, a preferred method using a glucan preparation suitable for intravenous administration.

Since ischemia-reperfusion injury may follow trauma injury and most likely will occur following cardiac arrest, the present invention also provides bulk-packaged or individually-packaged injectable or intravenous solutions suitable for administration by emergency medical personnel at the site of trauma injury or cardiac arrest, as well as sterile powders suitable for preparing intravenous solutions.

(1→3)-β-D-Glucan Therapy for Treatment in Congestive Heart Failure and Related Cardiomvovathies Tumor necrosis factor (TNFα) is involved in dilated cardiomyopathy, myocyte apoptosis, transmural myocarditis, and biventricular fibrosis. TNFα has also been proposed to play a role in the pathology of congestive heart failure. In patients with chronic heart failure, decreased plasma TNFα levels have been shown to improve heart function (Liu, L. el al., *Int. J. Cardiol.* (1999) 69(1): 77–82; Oral, H. et al., *Clin. Cardiol.* (1995) 18(9 Suppl. 4) IV 20–27). The inventors have demonstrated that (1→3)-β-D-glucans significantly decrease TNFα levels, providing a novel therapy for congestive heart failure and related cardiomyopathies.

In patients who experience congestive heart failure, heart function can be improved by administration of one or more (1→3)-β-D-glucan(s) in the method of the present invention, the dosage being administered intravenously, intramuscularly, intraperintoneally, subcutaneously, intradermally, or orally in an amount effective to deliver from about 1 mg/kg to about 150 mg/kg of the one or more (1→3)-β-D-glucans to the patient. Appropriate protocols for glucan administration to a patient experiencing congestive heart failure should be determined by the patient's individual physician. Dosage calculation and timing are determined by techniques known to those of skill in the medical arts.

(1→3)-β-D-Glucan Therapy for Sequelae of Viral Infection

Viral infection has been associated with a variety of sequelae resulting in tissue damage. For example, a high rate of unexpected left ventricular (LV) dysfunction has been observed in human immunodeficiency virus (HIV)-infected patients (Herskowitz et al., *Am. J. Cardiol.* (1993) 71: 955–958), and myocardial involvement has been associated with early stage HIV infection (Coudray, N. et al. *Eur. Heart J.* (1995) 16: 61–67). Pathogenesis has also been associated with the inflammatory response to the virus. For example, NFκB has been associated with virus-induced apoptosis of cells, and treatment of cells with oligonucleotide decoys that bind NFκB have been shown to protect AT-3 cells from Sindbis virus-induced apoptosis (Lin, K-I et al. *J. Cell Biol.* (1995) 131: 1149–1161). TNFα induction associated with reovirus, murine hepatitis virus, and murine cytomegalovirus has been demonstrated to play a pathogenic role in the development of liver disease. Studies have demonstrated that the inflammatory responses can be separated from conditions of significant hepatic damage at early times during viral infections and have shown that endogenous cytokine contributes to virus-induced liver disease (Orange, J. S. et al., *J. Virol.* (1997) 71(12): 9248–9258). Activated NF-κB has been shown to be required for reovirus-induced apoptosis (Connolly, J. et al., *J. Virol* (2000) 2981–2989). Other viruses also induce NF-κB activation. For example, the long terminal repeat (LTR) of human immunodeficiency virus (HIV) contains κB response elements, and activation of NF-κB has been shown to directly stimulate viral gene expression (Chen, B. K. et al., *J. Virol.* (1997) 71: 5495–5504; Chene, L. et al., *J. Virol.* (1999) 73: 2064–2073). The human T-cell leukemia Tax protein induces NF-κB activation (Beraud, C. and W. Green, *J. Acquired Immunodef. Syndr.* (1996) 13(Suppl. 1): S76–S84), while NF-κB activation induces expression of cellular genes that promote HTLV replication (Ballard, D. W. et al., *Science* (1988) 241: 1652–1655).

The present method provides a therapy for decreasing virus-induced tissue damage by decreasing levels of NFκB and TNFα which have been associated with tissue pathology. As TNFα is generally induced at early times post-infection, it is preferable to administer a dosage of from about 1 mg/kg body weight to about 150 mg/kg body weight to a patient at early stages of viral infection. The dosage can be administered systemically, by intravenous, oral, or parenteral means, or can be administered locally by injection at or near the site of infection.

(1→3)-β-D-Glucan Therapy for the Treatment of Bacterial Infection Sequelae and Sepsis The method of the present invention provides (1→3)-β-D-glucan administration to reduce tissue damage, mediated by pro-inflammatory cytokines such as NFκB and TNFα, during bacterial infection and especially during sepsis. Glucans are administered upon diagnosis of bacterial infection, particularly where the bacterial species is known to produce systemic infection or sepsis. Such bacterial species include, for example, *Staphylococcus aure us, Pseudomonas aeruginosa, Escherichia coli, Bacteroides fragilis* and *Yersinia enterocolitica*. Glucans can also be administered post-onset of sepsis to reduce septic sequelae, such as tissue necrosis. A dosage sufficient to deliver from about 1 mg/kg body weight to about 150 mg/kg body weight is administered either orally, parenterally, or intravenously to a patient with bacterial infection or sepsis.

(1→3)-β-D-Glucan Administration to Reduce Transplant Rejection

All forms of transplantation involve some ischemic and traumatic injury to the donor tissue, which has been proposed as one of the reasons for the early timing of most rejection episodes. By decreasing levels of NFκB and TNFα post-transplant, the donor tissue can be protected from much of the host immunoresponse involved in rejection. In the method of the present invention, a dosage sufficient to delivery from about 1 mg/kg body weight to about 150 mg/kg body weight is administered either orally, parenterally, or intravenously to a patient prior to or following organ transplantation. A preferred method of administration is intravenous administration.

An added benefit of the method of the present invention for potential heart transplant patients with congestive heart failure is the increased cardiac function associated with β-glucan administration. By improving cardiac function pre-transplant, β-glucan therapy can prolong the life of a CHF patient, while decreasing the probability of rejection once the donor heart is transplanted.

(1→3)-β-D-Glucan Administration to Prolong Gene Therapy

Inhibition of TNFα has been demonstrated to decrease inflammation and prolong adenovirus gene expression in lung and liver in gene therapy protocols (Zhang, H. G. et al. (1998) 9 (13): 1875–1884). Results from these studies demonstrated that TNFα is the primary factor involved in elimination of adenovirus-infected cells in liver and lung. Results also indicated that inhibition of TNFα prolonged the viral infection, allowing more time for delivery of the target gene. The method of the present invention provides a novel therapeutic method for prolonging effective gene therapy by decreasing TNFα levels using (1→3)-β-D-glucan administration.

In the method of the present invention, (1→3)-β-D-glucan administration is begun at onset of the gene therapy protocol (infection with the viral vector). A dosage of from about 1 mg/kg body weight to about 150 mg/kg body is administered either orally, parenterally, or intravenously. A preferred route of administration is intravenous administration. The (1→3)-β-D-glucan dosage can be delivered either systemically or locally, although the preferred method of administration is systemic administration.

Glucan Treatment for Spinal Cord Ischemia or Ischemia of a Limb

Spinal cord ischemia with resulting paraplegia can result from transient occlusion of the thoracic aorta, and studies have shown that ischemia preconditioning can protect against paraplegia (Abraham, V. S. et al., *Ann. Thorac. Sure.*

(2000) 69(2): 475–479.) The present invention provides a method for preventing and treating spinal cord injury resulting from ischemia. A therapeutic dosage of (1→3)-β-D-glucan, as described previously, can be delivered by means known to those of skill in the art, including intravenous or oral administration, as well as by direct injection into the injured tissue. Delivery of the appropriate therapeutic dosage can be made after onset of ischemia, or, especially in the case of surgical occlusion of the thoracic aorta, prior to onset of ischemia.

Ischemia of the tissues of an arm or leg in the human, or a fore- or hindlimb in a mammal, can also result from dissection or occlusion of an artery which supplies blood to those tissues. The present invention provides a means for decreasing ischemic injury to the limb tissue by providing a therapeutic dosage of (1→3)-β-D-glucan to the tissue either prior to onset of ischemia, particularly where it is a requirement for a surgical procedure, or after onset of ischemia, which may accompany traumatic injury. The therapeutic dosage can be delivered intravenously, orally, parenterally, or by direct injection at the site of the ischemic injury.

The invention will be further described by reference to the following detailed examples.

EXAMPLE 1

Effect of (1→3)-β-D-Glucan Treatment in Sepsis

Age- and weight-matched male ICR/HSD mice were obtained from Harlan Sprague-Dawley (Indianapolis, Indiana) and maintained on standard laboratory chow with water ad libitum and a 12-hour light-dark cycle. Mice were determined to be virus free by serologic testing. Glucan phosphate and scleroglucan were prepared and characterized as described by Williams et al. (Carbohyd. Res. (1991) 219: 203–213), Pretus et al. (J. Pharmacol. Exp. Ther. (1991) 257: 500–10), and Lowman et al. (Carbohydr. Res. (1998) 306: 559–562), as well as U.S. Pat. No. 4,739,046 (DiLuzio, Apr. 19, 1988), U.S. Pat. No. 4,761,402 (Williams et al., Aug. 2, 1988), U.S. Pat. No. 4,818,752 (Williams et al., Apr. 4, 1989), U.S. Pat. No. 4,833,131 (Williams et al., May 23, 1989), U.S. Pat. No. 4,900,722 (Williams et al., Feb. 13, 1990), and U.S. Pat. No. 4,975,421 (Williams, et al., Dec. 4, 1990), each of which is incorporated herein by reference.

Glucan phosphate has been shown to specifically bind to the macrophage (1→3)-β-D-Glucan receptor with an affinity of 24 $\mu$mol/L (low affinity), whereas scleroglucan specifically binds the (1→3)-β-D-glucan receptor with an affinity of 11 nmol/L (high affinity).

Nuclear extracts were prepared by homogenizing tissue in hypotonic buffer containing protease inhibitors and incubating the homogenates on ice for approximately 30 minutes with gentle agitation. After cells were lysed, nuclei were collected by centrifugation (14,000 revolutions/min for 5 minutes). Nuclear proteins were extracted by incubating the nuclear fraction on ice for 30 minutes in hypertonic salt buffer containing protease inhibitors. Nuclear extract supernatant was harvested after centrifugation, then stored at −80° C. Protein was quantified by the BCA microprotein assay (Pierce, Rockford, Ill.).

The electrophoretic mobility shift assay (EMSA) was performed using double-stranded consensus binding site oligonucleotides for NF-κB and NF-IL6 (C/EBP, CCAAT enhancer binding protein), obtained from Santa Cruz Biotechnology (Santa Cruz, Calif.). Oligonucleotides were end-labeled with [$\gamma$-$^{32}$P]-labeled adenosine triphosphate (Amersham, Arlington Heights, Ill.) with T4 polynucleotide kinase (Promega, Madison, Wis.), using methods known to those of skill in the art. Binding assays were performed in 10 µl of binding reaction mixture containing 10 µg of nuclear proteins and [γ-$^{32}$P]-labeled NF-κB or NF-IL6 oligonucleotides. The binding reaction mixture was incubated at room temperature for 20 minutes, then electrophoresed on 4% non-denaturing polyacrylamide gel electrophoresis (PAGE) gels. Specificity of binding was confirmed by addition of a 10-fold excess of cold oligonucleotide to separate reaction mixtures. A 10-fold excess of cold oligonucleotide containing the AP-1 binding site was added to separate reaction mixtures as an additional control. After PAGE, gels were dried and exposed to Kodak X-omat® film at −70° C. Autoradiograms were quantified by scanning densitometry with a Sun IPC workstation running Bioimage® software (Millipore, Bedford, Mass.).

Cytokine reverse transcriptase-polymerase chain reaction (RT-PCR) assays were performed using standard techniques known to those of skill in the art. Upstream and downstream primers for murine TNF-α and IL-6 were used to detect presence of those cytokines. Reduced glyceraldehyde phosphate dehydrogenase (GAPDH) was used as the gene transcript control.

In studies of (1→3)-β-D-glucan effects on tissue damage due to sepsis, blood (~0.3 ml) was obtained by open heart puncture from groups of 3 ICR/HSD mice subjected to cecal ligation and puncture (CLP), performed according to the method of Baker et al., *Suryery* (1983) 94: 331–335, as described by Ayala et al., Circ. Shock (1992) 36: 191–199. Mice subjected to laparotomy only (LO) served as surgical and anesthesia controls. Negative controls were not subjected to either procedure. Blood samples were collected from each group at 1, 2, 4, 8, and 24 hours after surgery. Samples were inoculated into prereduced anaerobically sterilized chopped meat carbohydrate broth (Carr-Scarborough, Stone Mountain, Ga.) under a constant stream of anaerobic carbon dioxide in a VPI Inoculator (Bellco Glass, Vineland, N.J.). After mixing, 1 ml of inoculated broth was aseptically removed from each 6-ml rubber-stoppered anaerobic tube into a sterile loose-capped aerobic culture tube. Both aerobic and anaerobic culture tubes were incubated at 37° C. for 72 hours.

Samples (0.1 ml) from anaerobic tubes were streaked for isolation on anaerobic laked blood agar plates (LBAP), aerobic 5% sheep blood agar (SBAP), and MacConkey agar plates (MAC) to recover all aerobic and facultative bacterial species. Samples (0.1 ml) from aerobic tubes were streaked on MAC to recover strictly aerobic gram-negative rods, which do not grow in anaerobic broth. SBAP and MAC plates were incubated in an aerobic environment, while LBAP plates were incubated in an anaerobe jar with BBL GasPak® Anaerobic System envelope and palladium catalyst (Becton-Dickinson, Cockneysville, Maryland) at 37° C. After 48 hour incubation, each colony type was counted, gram stained, and subcultured on aerobic and anaerobic plates under appropriate atmospheric conditions for 24 hours. Organisms that grew only on anaerobic plates were identified as strict (obligate) anaerobes and presumptively; speciated by gram stain morphologic characteristics, the presence or absence of pigment on LBAP, catalase, indole, and esculin reactions, as well as sugar fermentation profiles. Facultative anaerobes, as well as obligate aerobes were similarly identified using growth requirements and standard methods of identification as listed above.

In pretreatment protocols, 45 mice were randomly divided into 3 groups of 15 mice per group. Group 1 received isovolumetric saline solution intraperitoneally 1 hour before CLP. Group 2 received glucan phosphate (1 mg/mouse=50 mg/kg, intraperitoneally) 1 hour prior to CLP. Group 3 received scleroglucan (1 mg/mouse=50 mg/kg, intraperitoneally) 1 hour prior to CLP. To assess tissue transcription factor activation and cytokine messenger RNA (mRNA) levels, liver and lung tissue were harvested from 5 mice per group at 3 hours after surgery. The remaining 10 mice in each group were observed for pathology and mortality. Laparoscopy-only (LO) controls and negative controls received the same saline, glucan phosphate, and scleroglucan treatment as CLP mice.

In post-treatment protocols, 30 mice were subjected to CLP. These 30 mice were then randomly divided into 2 groups of 15 mice per group. Group 1 received isovolumetric saline solution intravenously 15 minutes post surgery. Group 2 received glucan phosphate (1 mg/mouse=50 mg/kg, intravenously) 15 minutes postsurgery. To assess tissue transcription factor activation and cytokine mRNA levels, liver and lung tissue were harvested from 5 mice per group at 3 hours post surgery. The remaining 10 mice in each group were followed for pathology and mortality. LO and negative controls received the same treatments. Tissues were snap frozen and stored in liquid nitrogen until assayed.

Survival trends were compared with the Cox proportional hazard and log-rank procedures. Transcription factor and cytokine mRNA integrated intensities were normalized to the untreated control group, which was set at 1.0. Figures illustrate group mean±SEM responses for LO and CLP at each time point. Analysis of variance (ANOVA) was used to compare group means and to assess the effects of CLP versus laparoscopy and time. Individual pairwise comparisons were performed with the least-significant difference procedure (if ANOVA F test was significant) or Tukey's procedure (if the ANOVA F test was not significant). Differences in bacteremia between LO and CLP groups were assessed with exact probability level determinations. Each protocol was repeated 3 times. A probability of 0.05 or less was used to indicate statistical significance.

Figure 2:
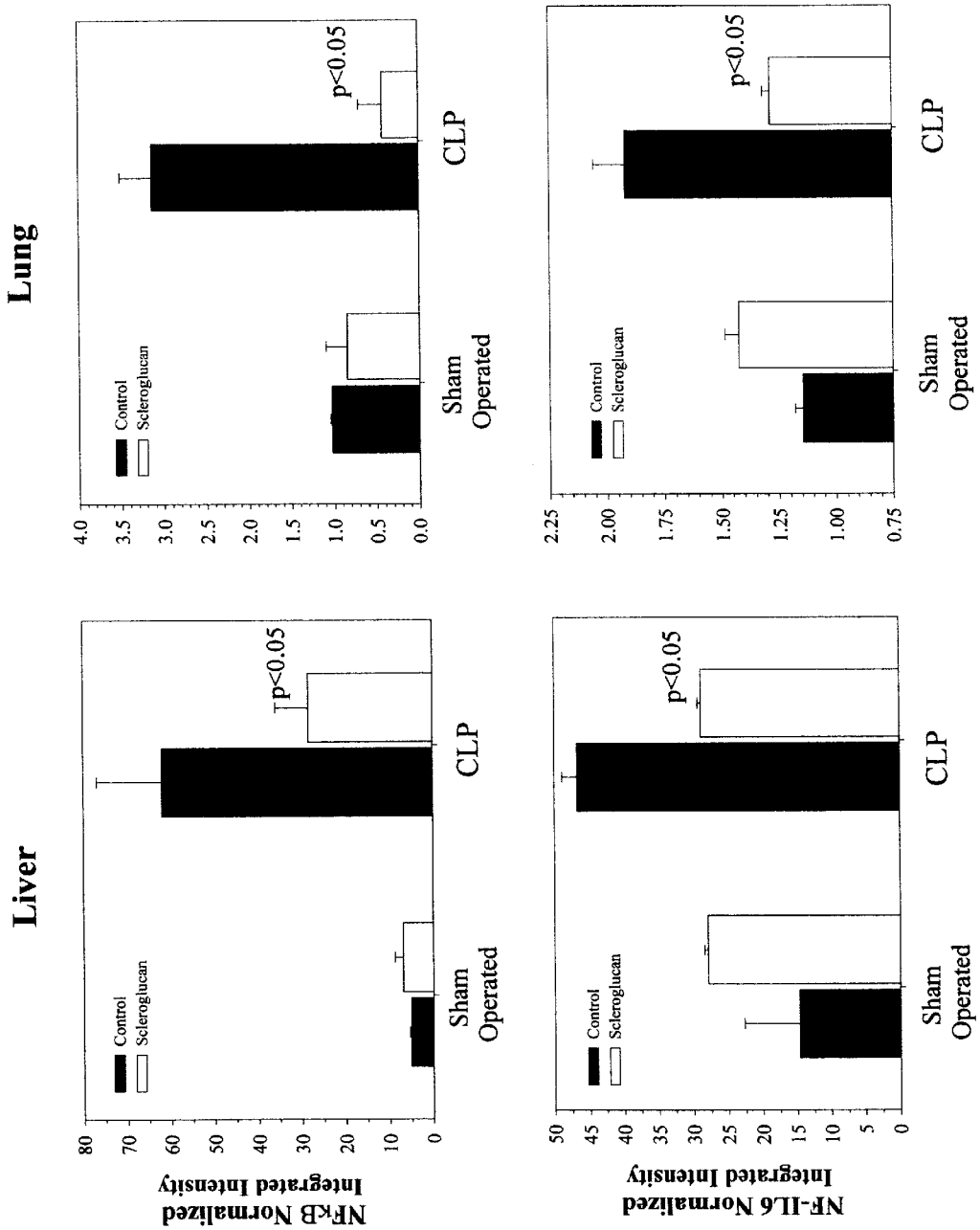
FIG. 2 illustrates results of scanning densitometry of autoradiograms derived from gel shift assays. Tissue samples were harvested 3 hours subsequent to CLP. NF-κB and NF-IL6 nuclear binding activity in liver and lung tissue were decreased in mice pretreated with scleroglugan (50 mg/kg, injected intraperitoneally). Results are shown as normalized integrated intensity for binding activity in liver and lung tissue taken from mice subjected to CLP and to laparotomy only (LO).

Pretreatment With (1→3)-β-D-Glucans Decreased Tissue NF-κB and NF-IL6 Levels After Induction of Polymicrobial Sepsis As shown in FIG. 1 and FIG. 2, intravenous administration of glucan phosphate or scleroglucan (50 mg/kg body weight) 1 hour before CLP resulted in a significant reduction in nuclear binding activity of liver and lung NF-κB and NF-IL6. Liver and lung NF-κB and NF-IL6 nuclear binding activity were increased 3 hours after CLP compared with LO ($P<0.05$). Glucan phosphate pretreatment (50 mg/kg body weight) inhibited NF-κB and NF-IL6 nuclear binding activity in liver and lung 3 hours after CLP compared with the CLP control (FIG. 1). Glucan phosphate pretreatment decreased liver NF-κB and NF-IL6 binding activity by 58% and 77% ($P<0.05$), respectively (FIG. 1). Glucan phosphate pretreatment decreased lung NF-κB and NF-IL6 binding activity by 81% and 68% ($P<0.05$), respectively (FIG. 1).

The effect of scleroglucan pretreatment on liver and lung transcription factor activation is shown in FIG. 2. Scleroglucan pretreatment (50 mg/kg body weight) inhibited NF-κB and NF-IL6 nuclear binding activity in liver and lung 3 hours after CLP compared with the LO group (FIG. 2). Scleroglucan pretreatment decreased liver NF-κB and NF-IL6 binding activity by 54% and 38% ($P<0.05$), respectively (FIG. 2).

Pretreatment of CLP Mice With (1→3)-β-D-Glucan Increases Long-Term Survival

Figure 3:
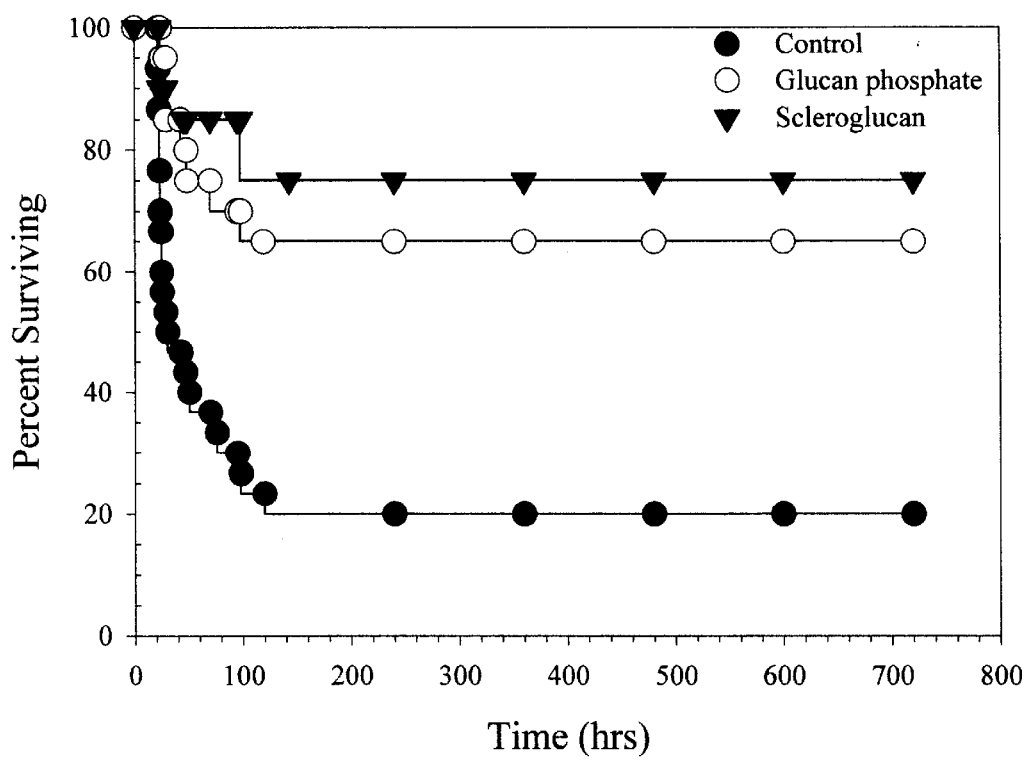
FIG. 3 illustrates survival rate, expressed as percentage surviving (Y axis) over time course (X axis), of mice subjected to CLP with or without glucan pretreatment (n≧20). Glucans were administered intraperitoneally (50 mg/kg) 1 hour prior to CLP surgery. Results are shown for control (CLP with no glucan treatment), glucan phosphate (glucan phosphate pretreatment followed by CLP), and scleroglucan (pretreatment with scleroglucan, followed by CLP).

Induction of polymicrobial sepsis by CLP resulting in an 80% mortality rate within 96 hours (FIG. 3), with the first death was observed 28 hours after surgery. Administration of either glucan phosphate or scleroglucan (50 mg/kg, intraperitoneallyl 1 hour before CLP increased long-term survival (FIG. 3). A single prophylactic injection of glucan phosphate resulted in a 65% ($P<0.001$) long-term survival rate (FIG. 3). In contrast, control mice subjected to CLP showed a median survival time of 28 hours and a 20% long-term survival rate (FIG. 3). No difference was noted between glucan treatment groups.

Figure 4:
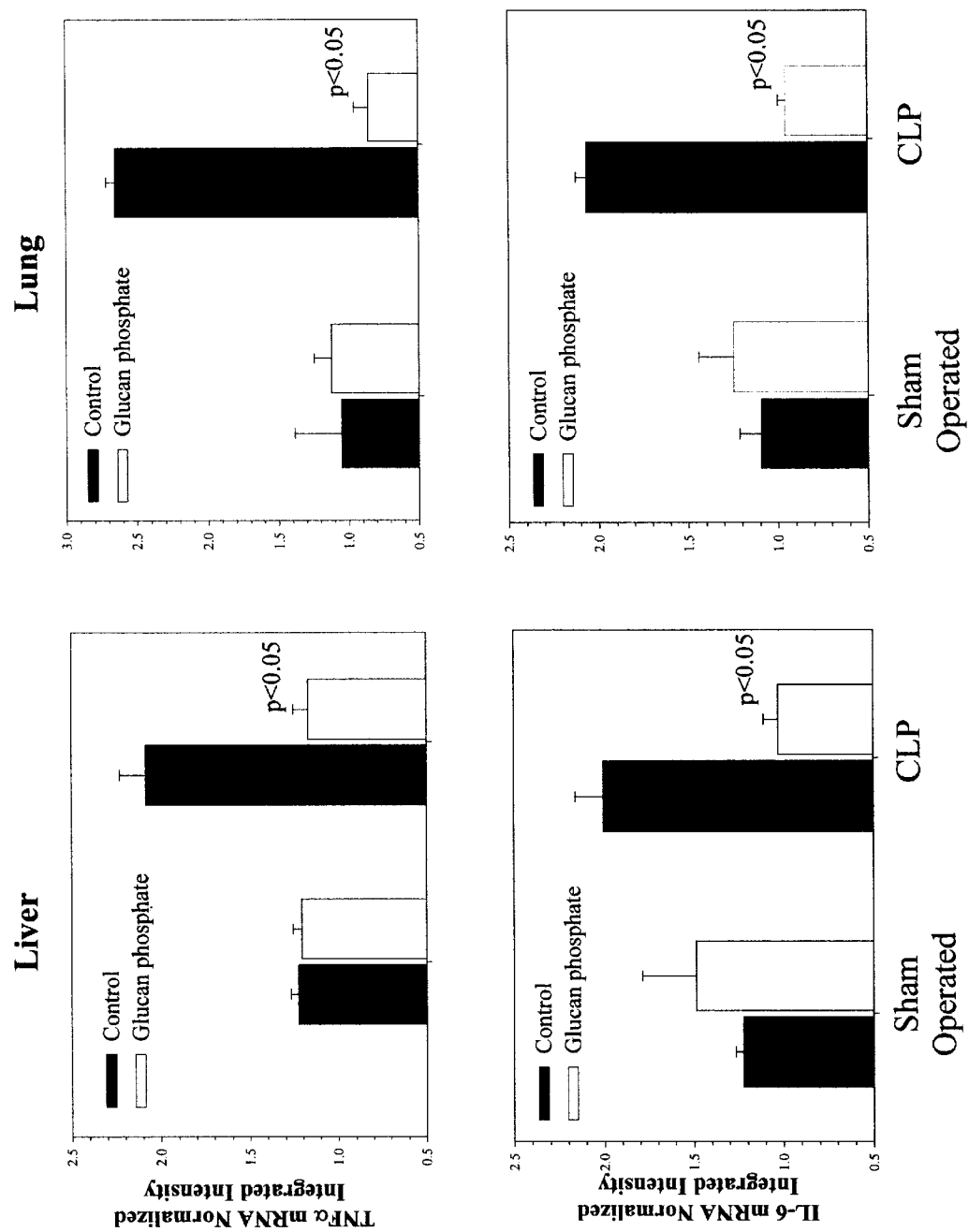
FIG. 4 illustrates normalized integrated intensity for mRNA levels assessed by RT-PCR and quantified by scanning densitometry. Tissue samples were harvested 3 hours after CLP or LO. TNF-α and IL-6 mRNA levels were measured in liver and lung tissue of ICR/HSD mice (n=4) pretreated with glucan phosphate (50 mg/kg, injected intraperitoneally), or saline solution (Control) before CLP or LO.

(1→3)-β-D-Glucan Pretreatment Decreases Tissue TNF-α and IL-6 mRNA Levels After Induction of Polymicrobial Sepsis TNF-a and IL-6 mRNA levels in liver-and lung were assessed by RT-PCR and subsequent densitometric analysis of the gel products. Because both the glucans showed comparable effects on survival and inhibition of transcription factor activation, only glucan phosphate was used for the remainder of the protocols. FIG. 4 illustrates the integrated intensities of cytokine mRNA levels. CLP increased TNF-α and IL-6 mRNA levels 3 hours after surgery. Glucan phosphate inhibited CLP-induced up-regulation of TNF-α and IL-6 mRNA in both liver and lung. Glucan phosphate pretreatment suppressed hepatic TNF-α and IL-6 mRNA levels by 44% and 49% respectively ($P<0.05$), relative to CLP controls (FIG. 4). In both liver and lung, glucan phosphate pretreatment maintained tissue cytokine message in CLP mice at levels not noted to be significantly different from-those of LO mice.

Figure 5:
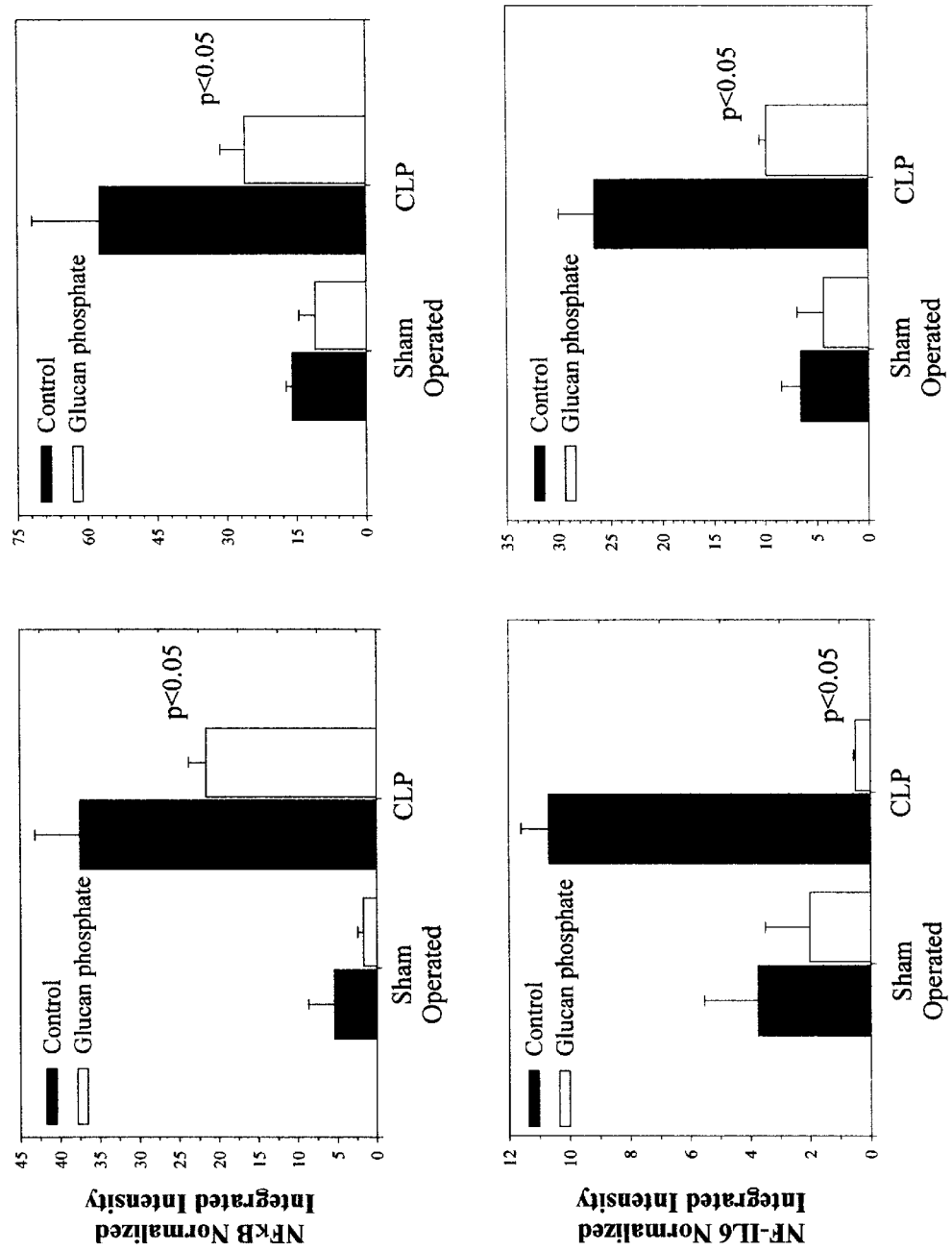
FIG. 5 is a graphic representation of scanning densitometry quantification of autoradiograms of gel shift assays for NF-κB and NF-IL6 nuclear binding activity in liver and lung tissue for ICR/HSD mice subjected to either CLP or LO. Mice were treated with glucan phosphate (50 mg/kg, administered intravenously) 15 minutes after surgery, or saline solution (Control).

Glucan Phosphate Posttreatment Decreases Tissue NF-κKB and NF-IL6 Levels After Induction of Polymicrobial Sepsis Glucan phosphate (50 mg/kg) was intravenously administered 15 minutes after CLP. As in pretreatment protocols, liver and lung NF-κB and NF-IL6 nuclear binding activity were increased 3 hours after CLP relative to the LO controls ($P<0.05$) (FIG. 5). Intravenous glucan phosphate administration (50 mg/kg) inhibited NF-κB and NF-IL6 nuclear binding activity in liver and lung 3 hours after CLP compared with CLP control (FIG. 5). Glucan phosphate treatment decreased liver NF-κB and NF-IL6 binding activity by 42% and 95%, respectively ($P<0.05$) (FIG. 5). Glucan phosphate treatment decreased lung NF-κB and NF-IL6 binding activity by 54% and 63%, respectively ($P<0.05$) (FIG. 5).

Figure 6:
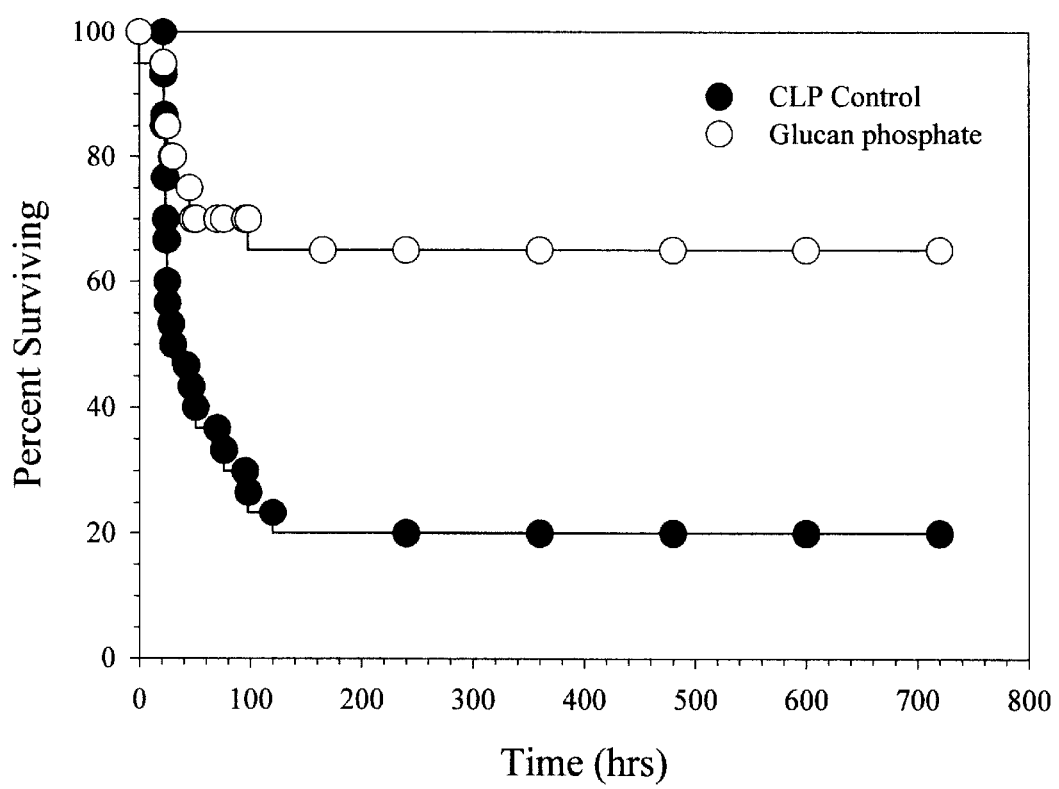
FIG. 6 graphs percentage survival (Y axis) over time course (X axis) for mice subjected to CLP and subsequently treated with glucan phosphate (50 mg/kg, administered intravenously 15 minutes post surgery) or saline solution (Control). ICR/HSD mice subjected to CLP all developed polymicrobial sepsis. However, as indicated, glucan phosphate treatment significantly (P<0.05) increased survival rate. n≧20 per group.

Glucan Phosphate Posttreatment Increased Survival in Mice with Polymicrobial Sepsis Induced by CLP Administration of glucan phosphate 15 minutes (50 mg/kg; intravenously) after CLP increased long-term survival (FIG. 6). A single posttreatment injection of glucan phosphate produced a 65% long-term survival rate ($P<0.001$) (FIG. 6). In contrast, control mice subjected to CLP without glucan phosphate treatment exhibited a 20% long-term survival rate and a median survival time of 28 hours (FIG. 6).

Figure 7:
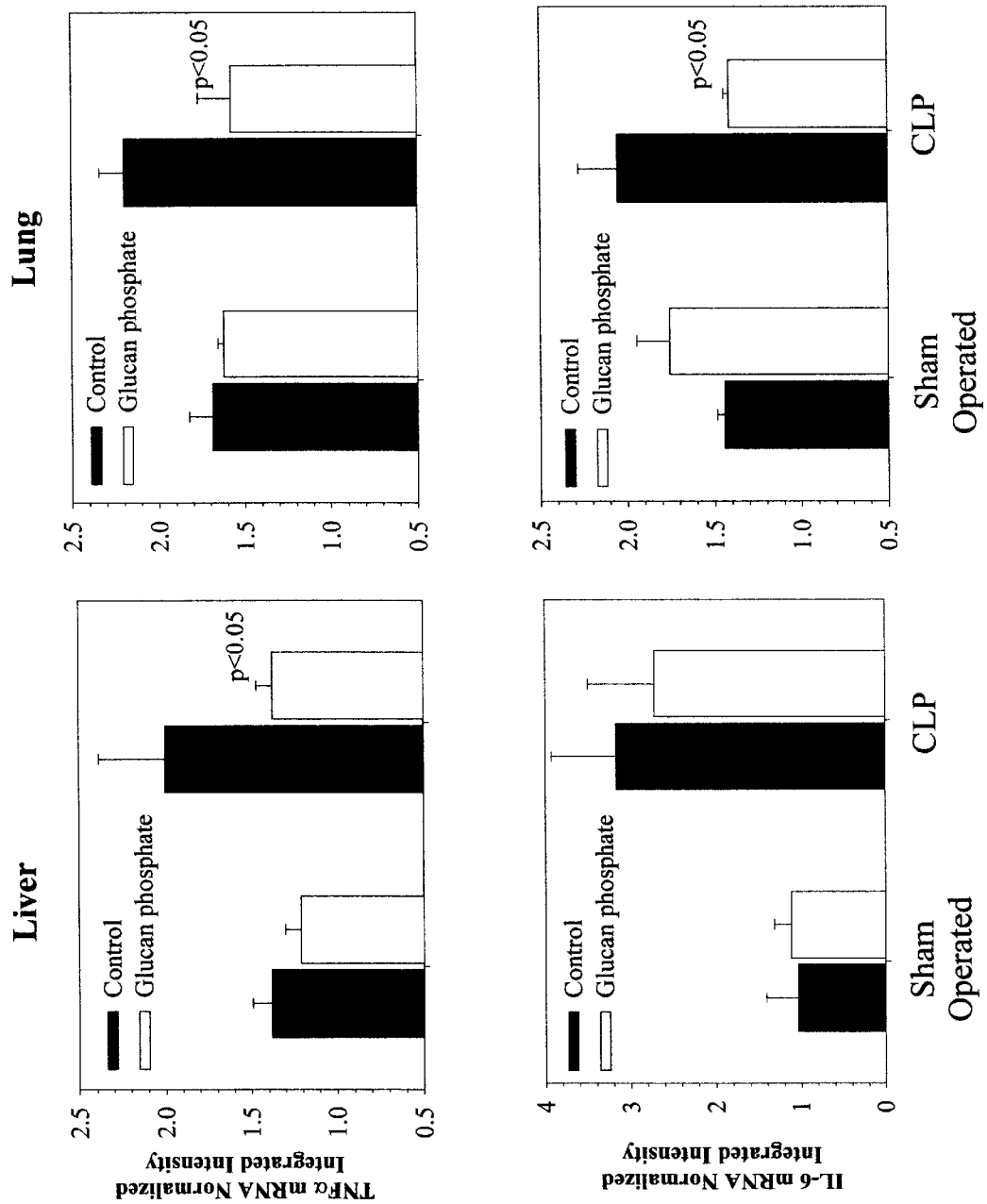
FIG. 7 is a series of graphs illustrating RT-PCR data, quantified by scanning densitometry, for TNF-α and IL-6 mRNA levels in liver and lung tissue of ICR/HSD mice subjected to LO or CLP and treated with glucan phosphate (50 mg/kg, administered intravenously) or saline solution (Control) 15 minutes post surgery. As indicated, glucan phosphate treatment suppressed hepatic TNF-α mRNA levels by 31% (P<0.05) relative to CLP controls. Glucan phosphate treatment suppressed lung TNF-α and IL-6 mRNA levels by 28% and 30% (P<0.05) relative to CLP controls.

Glucan Phosphate Posttreatment Decreases Tissue TNF-α and IL-6 mRNA Levels After Induction of Polymicrobial Sepsis FIG. 7 illustrates the integrated intensities of TNF-α and IL-6 mRNA levels in liver and lung of LO and-CLP mice treated with glucan phosphate 15 minutes after surgery. Glucan phosphate treatment significantly inhibited CLP-induced up-regulation of TNF-α and IL-6. Glucan phosphate posttreatment suppressed hepatic TNF-α message levels by 31% relative to CLP controls ($P<0.05$).(FIG. 7). Hepatic IL-6 mRNA levels were not altered in the treatment group (FIG. 7). Glucan phosphate treatment suppressed lung TNF-α and IL-6 message levels by 28% and 30%, respectively, relative to CLP controls ($P<0.05$) (FIG. 7).

EXAMPLE 2

Effects of Glucan Treatment on Ischemia/ Reperfusion Injury

Ischemia/reperfusion protocols were performed using Sprague-Dawley rats (Harlan Sprague-Dawley, Indianapolis, Indiana). Left anterior descending (LAD) coronary artery occlusion was performed by tying off the LAD artery near its origin using a suture. Glucan phosphate was employed in the ischemia reperfusion (I/R) studies.

(1→3)-β-D-Glucans Significantly Reduced Infarct Size and Area at Risk in Rat Hearts.

Figure 8:
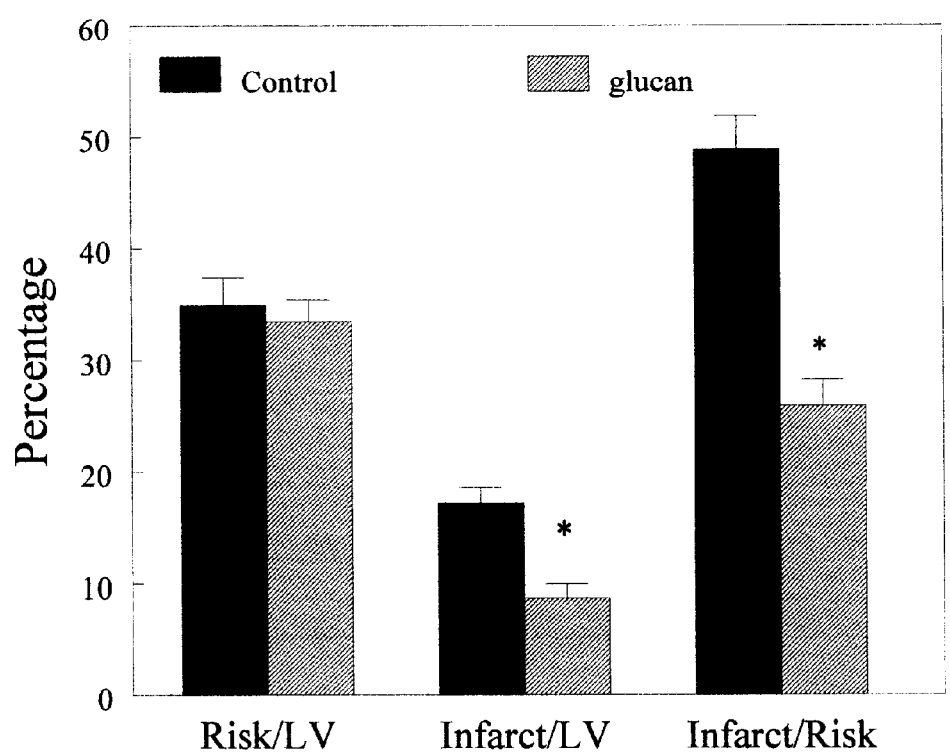
FIG. 8 is a graph of infarct size, as determined by triphenyltetrazolium chloride (TTC) staining, in rats treated with the experimental protocol, illustrating the effects of (1–3)-β-D-glucan on myocardial infarction in rats. Rats were pretreated with glucan for i one hr. before the hearts were subjected to ischemia for 45 min., followed by reperfusion for 4 hr. Areas of left ventricle (LV), risk area (RA), and infarct area (IA) were scanned and analyzed by imaging as described in the Examples. Values are expressed as means±SEM of 8–10 rats from each group (P<0.05).

Sprague-Dawley rats (250–300 g) were treated, with (1→3)-β-D-glucans at a concentration of 40 mg/kg one hour before the hearts were subjected to 45 minutes of occlusion of the left anterior descending (LAD) coronary artery, followed by reperfusion for 4 hours. At the completion of the experimental protocol, the heart was removed, rinsed free of blood, stained with 1% Evans Blue, and sectioned into five slices, followed by incubation in triphenyltetrazolium chloride (TTC) solution. Viable myocardium (risk area) was stained with TTC while the necrotic myocardium was pale white. The area of infarction on both sides of each slice was analyzed by an image analyzer (Alpha Imager 2000), corrected for each slice weight and summed for each left ventricle. The infarct areas were expressed as a percentage of risk area as well as a percentage of left ventricle and the risk areas were expressed as a percentage of left ventricle. As shown in FIG. 8, rats treated with glucan showed reduced infarct size/area at risk (25.86±2.33% v 48.82±3.03%), indicating that (1→3)-β-D-glucans prevent myocardial I/R injury.

Figure 9:
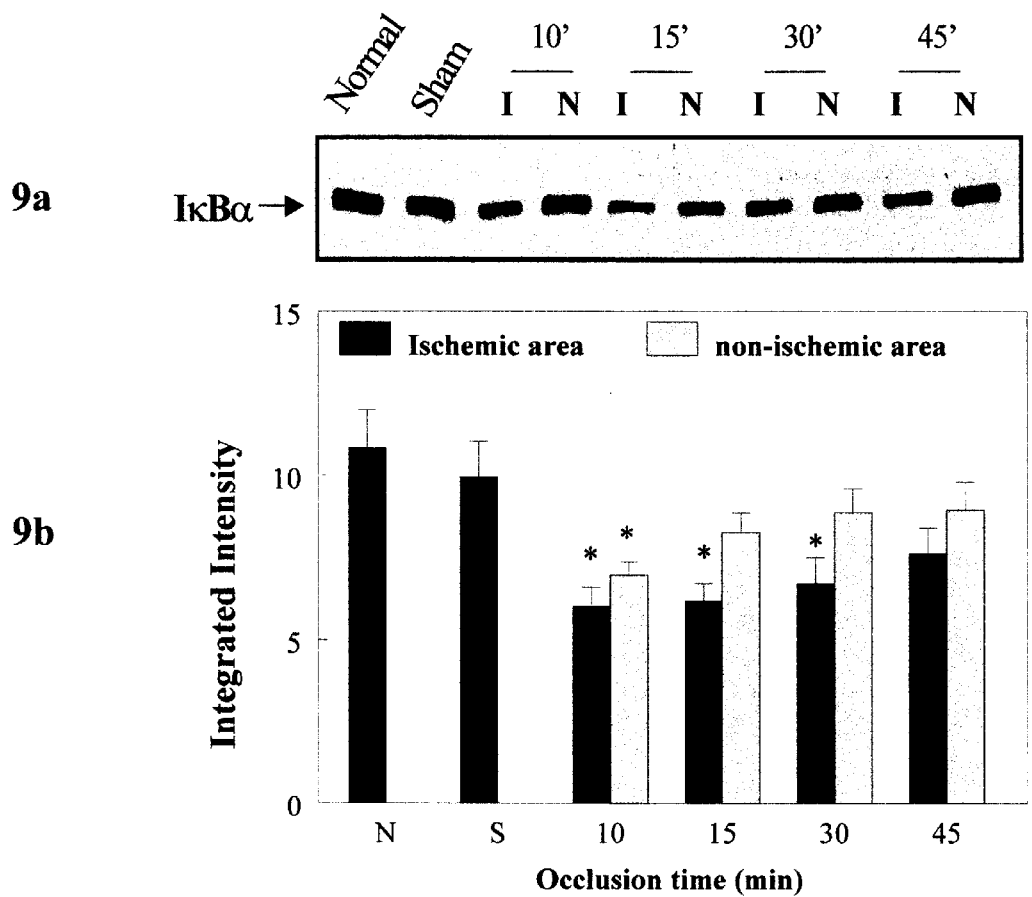
FIG. 9a and FIG. 9b illustrate levels of cytoplasmic IκBα in rat myocardium. Cytoplasmic proteins were isolated from rat hearts that had been subjected to ischemia for 10, 15, 30, and 45 min., respectively, and analyzed by Western blot (FIG. 9a). Blots were then subjected to image analysis. Results (FIG. 9b) are expressed as means±SEM of 5 hearts sampled at each time point for normal group (N) and sham group (S). Statistical significance is P<0.05 compared to normal group.
Figure 10:
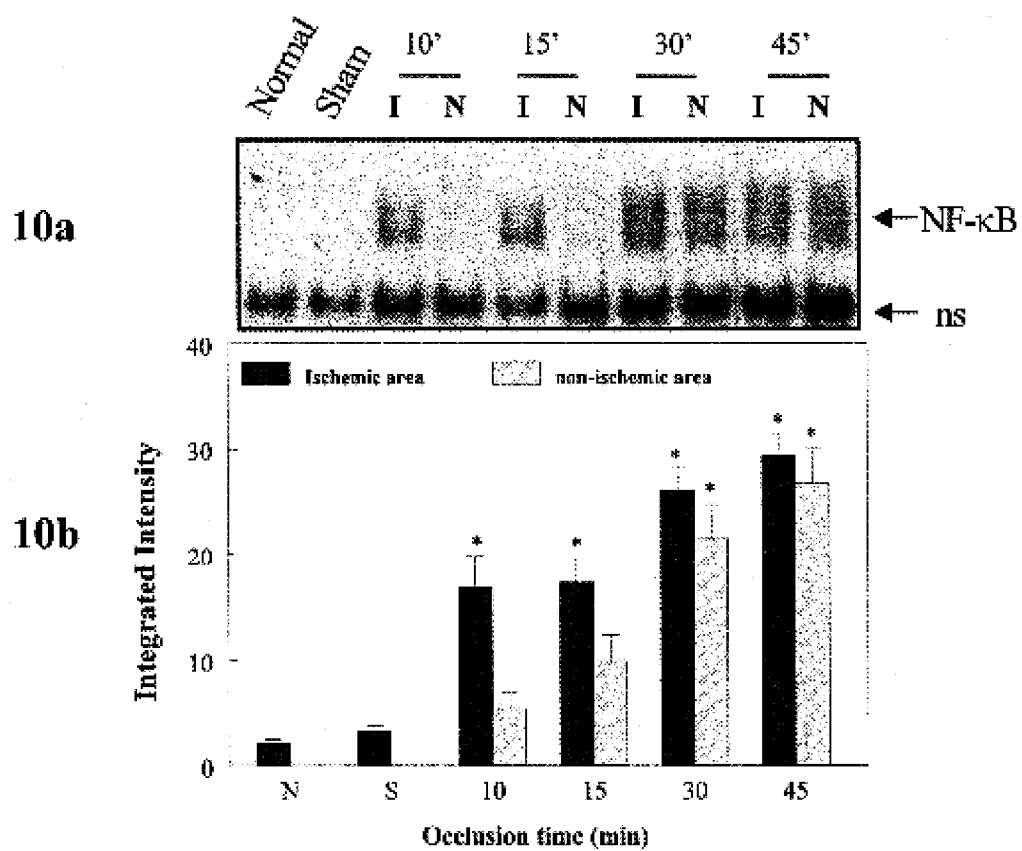
FIG. 10a and FIG. 10b are graphs of ischemia-induced NF-κB nuclear binding activity in in vivo rat myocardium. Nuclear proteins were isolated from rat hearts that had been subjected to ischemia for 10, 15, 30, and 45 min., respectively, then analyzed by electromobility shift assay (EMSA) (FIG. 10a). Results of image analysis (FIG. 10b) were expressed as means±SEM of 5 hearts sampled at each time point for normal group (N) and sham group (S). Non-specific binding is designated as "ns" and statistical significance is P<0.05 compared to normal (N).

Mechanism of action of (1→3)-β-D-Glucan Cardioprotective Effects: NF-κB Activation is Induced by Ischemia Through Rapid Activation of IKK, Resulting in Increased IκBα Protein Phosphorylation, Glucan Modulates the I/R-induced NF-κB Activation Previous studies performed by the inventors had shown that in vitro ischemia alone significantly induced NF-κB activation, while reperfusion increased the effects of ischemia. To investigate NF-κB activation in vivo, rat hearts were subjected to various periods of ischemia or ischemia and reperfusion (I/R). For example, levels of IκBα and phosphorylated IκBα proteins in cell cytoplasm following ischemia were evaluated by Western blot with anti-IκBα or antibody specific for the phosphorylated IκKα (FIG. 9a). NF-κB binding activity in the nucleus following onset of ischemia was analyzed by electrophoretic mobility shift assay (EMSA) (FIG. 10a). IκB kinase (IKK) activity was determined by immunoprecipitation with anti-IKK followed- by addition (of GST-IκBα substrate. Protein quantification was performed using the Bio-Rad-Molecular Imager® protocol (see FIG. 9b and FIG. 10b, which illustrate IκBα and NF-κB levels, respectively).

Figure 11:
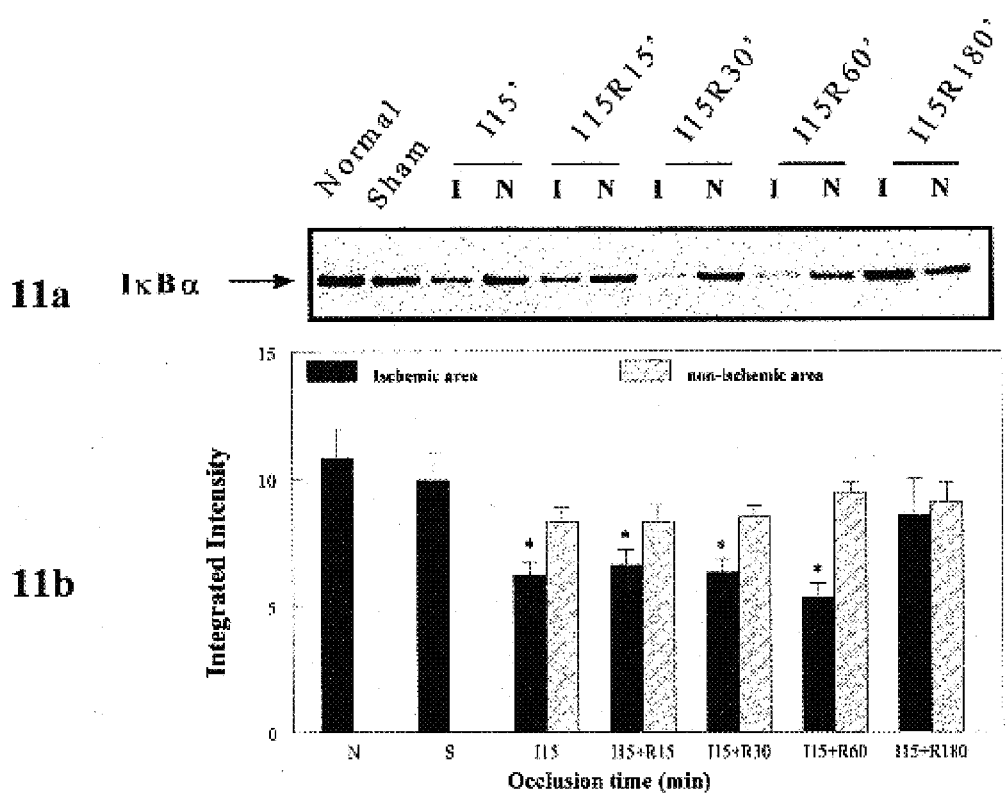
FIG. 11a and FIG. 11b are graphs of cytoplasmic IκKα protein levels in ischemic and non-ischemic areas of the heart after ischemia/reperfusion in in vivo rat hearts. Cytoplasmic proteins were isolated from rat hearts subjected to ischemia for 15 min., followed by reperfusion for 15, 30, 60, and 180 min., respectively. Isolated proteins were analyzed by Western blot (FIG. 11a) and image analysis (FIG. 11b). In the autoradiogram (FIG. 11a), "I" indicates ischemic area and "N" indicates non-ischemic area. Results were expressed as means±SEM of 5 hearts sampled at each time point for normal group (N) and sham group (S). P<0.05 compared to normal (N).

Following ischemia/reperfusion, cytoplasmic IκKα levels were also ascertained Cytoplasmic proteins were isolated from rat hearts subjected to ischemia for 15 min., followed by reperfusion for 15, 30, 60 and 180 min., respectively. Isolated proteins were analyzed by standard Western blotting techniques and image analysis; Results were expressed as means±SEM of 5 hearts sampled at each time point and graphed as shown in FIG. 11a and FIG. 11b.

Figure 12:
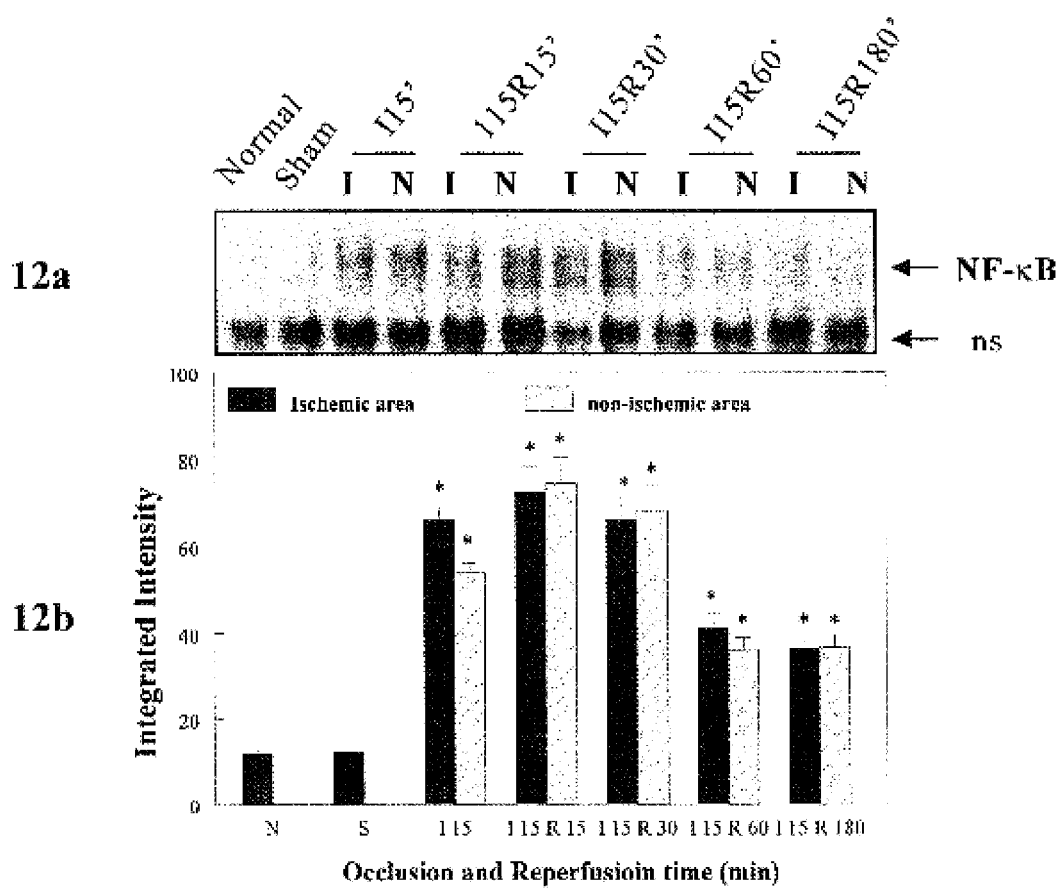
FIG. 12a and FIG. 12b graphically illustrate NF-κB nuclear binding activity in ischemic (I) and non-ischemic (N) rat myocardium after in vivo ischemia/reperfusion. Nuclear proteins were isolated from rat hearts which had been subjected to ischemia for 15 min., followed by 15, 30, 60, and 180 min. reperfusion, respectively. Samples were analyzed by EMSA. The graph is

NF-κB nuclear binding activity in rat myocardium after in vivo I/R was also determined. Nuclear proteins were isolated from rat hearts which had been subjected to ischemia for 15 min., followed by 15, 30, 60 and 180 min. reperfusion, respectively. Samples were analyzed by EMSA, as shown in FIG. 12a. Integrated intensity, expressed as means±SEM of 5 hearts sampled for each time point, is shown in FIG. 12b. The normal group is designated N, sham group as S, and non-specific binding is indicated as NS. $P<0.05$ as compared to normal (N).

Figure 13:
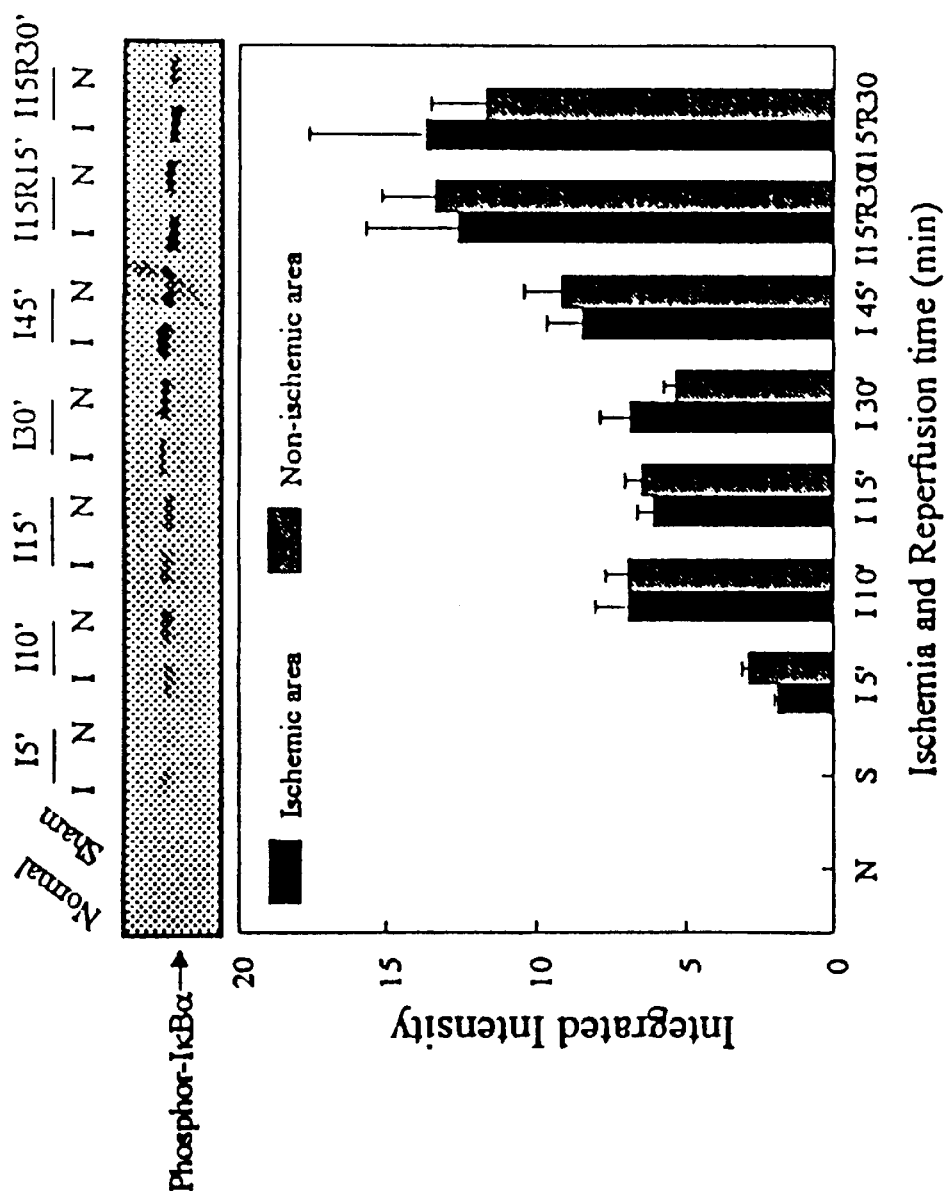
FIG. 13a and 13b illustrate levels of phosphorylated IκKα protein in cytoplasm of rat myocardium following ischemia/reperfusion. Cytoplasmic proteins were isolated from rat hearts that had been subjected to indicated periods of ischemia and reperfusion. Levels of phosphorylated IκKα protein were examined by Western blot with antiphosphor-IκBα (FIG. 13a). Phosphorylated IκBα proteins were undetectable in the hearts of normal (N) and sham (S) groups. Results of scanning densitometry are expressed as means±SEM of 5 hearts sampled at each time point (FIG. 13b).

Cytoplasmic IκKα protein levels were decreased, while nuclear NF-κB binding activity was increased, following 10 minutes of ischemia, with levels persisting for 30 to 45 minutes of ischemia. Reperfusion following 15 min. of ischemia augmented the ischemic effects. Levels of cytoplasmic phospho-IκBα were determined by Western blot. As shown in FIG. 13, 5 min. of ischemia increased the levels of phospho-IκBα, and longer periods of ischemia/reperfusion further increased the levels of phospho-IκBα, indicating the IκKα phosphorylation during ischemia/reperfusion contributes to activation of NF-κB.

Figure 14:
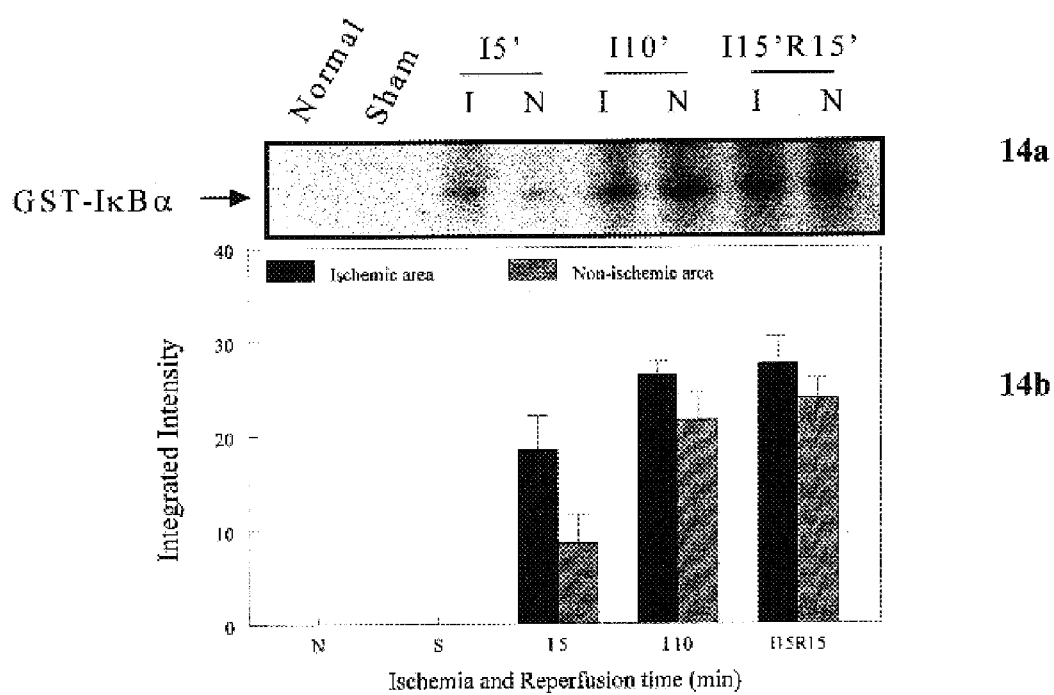
FIG. 14a shows an IκK kinase (IKK) assay and FIG. 14b is a graphic representation of the results of immunoprecipitation of IκK kinase (IKK) in ischemic and non-ischemic areas of rat myocardium which had been subjected to ischemia/reperfusion injury. Rat hearts were subjected to 5 min. (15') and 10 min. (10') of ischemia, as well as to 15 min. ischemia followed by 15 min. reperfusion (I15'R15'), as indicated. In the autoradiogram (FIG. 14a), "I" indicates ischemic area and "N" indicates non-ischemic area. Cytoplasmic proteins were isolated from each tissue sample and immunoprecipitated with anti-IKK, followed by addition of GST-IκBα substrate (FIG. 14a). IKK activity was undetectable in hearts of normal (N) and sham (S) groups (FIG. 14b). Results are expressed as means±SEM for 5 hearts at each time point.

Since IKK is key to IκKα phosphorylation, IKK activity was analyzed. As shown in FIG. 14, IKK activity was rapidly induced by 5 min. of ischemia and activity persisted for 10–15 min. after ischemia and reperfusion, indicating that NF-κB activation subsequent to ischemia/reperfusion is mediated by rapid induction of IKK activity, with a subsequent increase in IκKα phosphorylation.

Figure 15:
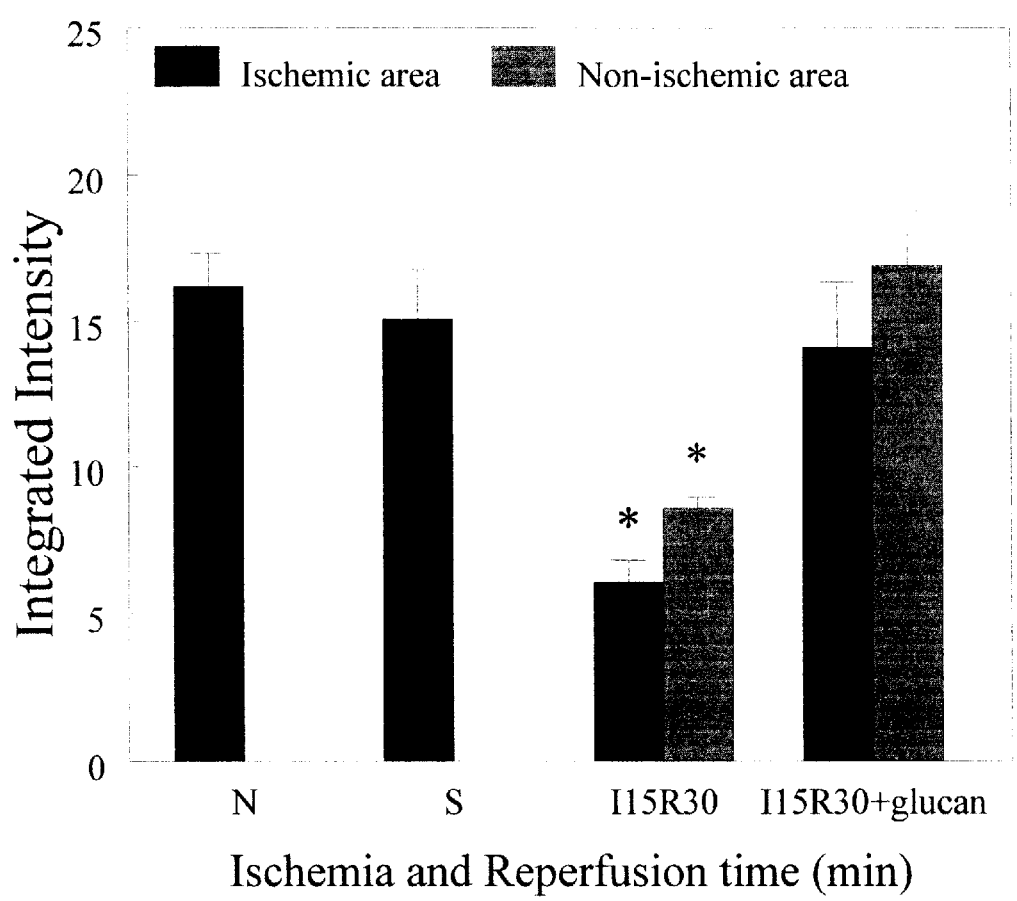
FIG. 15 is a graphic representation of effect of glucan on loss of IκBα from rat myocardial cytoplasm following I/R. Rats were pretreated with glucan (40 mg/Kg) for one hr. before being subjected to 15 min. of ischemia and 30 min. of reperfusion. Cytoplasmic proteins were isolated and levels of IκBα protein determined by Western blot analysis. Results were expressed as means±SEM for 5 hearts at each time point. P<0.05 as compared to normal (N).
Figure 16:
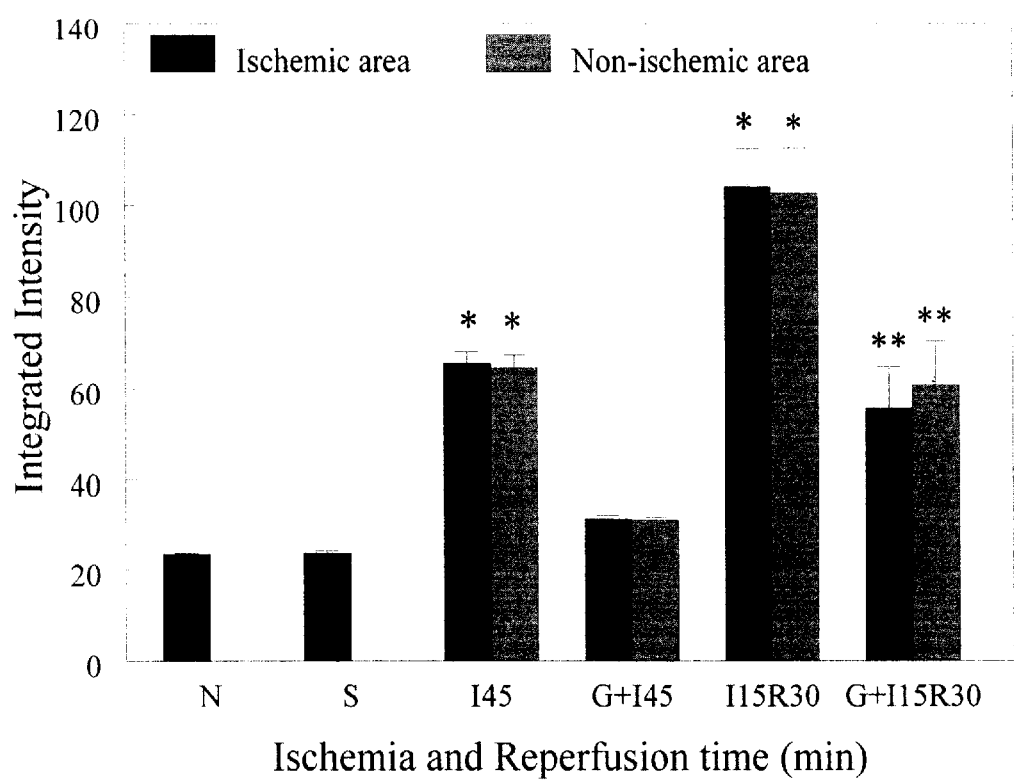
FIG. 16 graphically demonstrates the effect of glucan on nuclear NF-κB binding activity in rat myocardium subsequent to I/R. (Glucan decreases NF-κB binding activity in rat myocardium subsequent to I/R). Rats were pretreated with glucan (40 mg/Kg) for one hr. before being subjected to 45 min. of ischemia (I45), as well as 15 min. ischemia followed by 30 min. reperfusion (I15R30). Nuclear proteins were isolated and analyzed by EMSA. Results are expressed as means±SEM for 5 hearts at each time point. P<0.05 as compared to normal (N).

Glucan markedly reduced, but did not completely inhibit, I/R induced myocardial NF-κB binding activity in vivo. As demonstrated in FIG. 15 and FIG. 16, (1→3)-β-D-glucans prevent loss of cytoplasmic IκKα and reduce :nuclear NF-κB binding activity, indicating that (1→3)-β-D-glucans exert their post-I/R cardioprotective effects through regulation of NF-κB.

(1→3)-β-D-glucan Inhibits I/R-induced TNFα mRNA Expression

Figure 17:
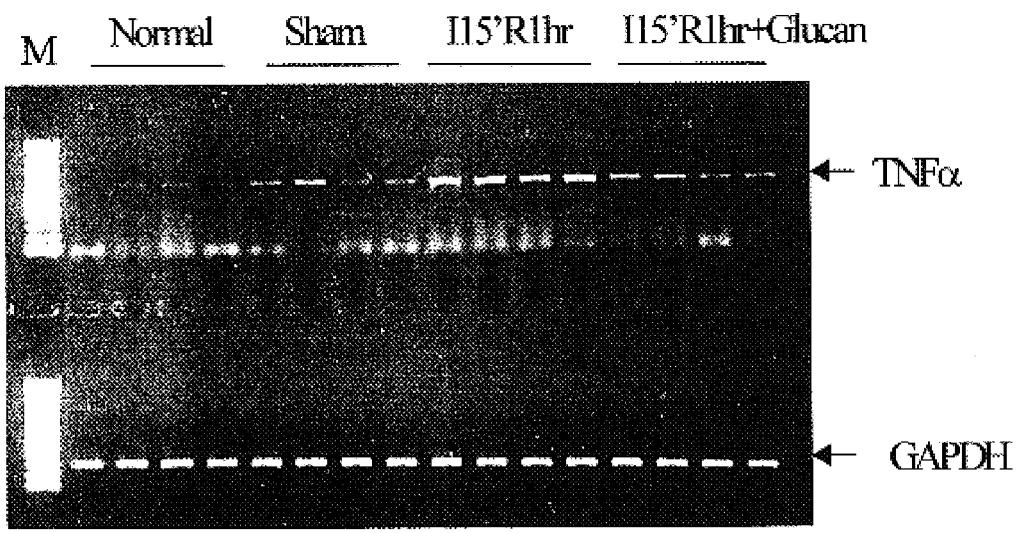
FIG. 17 depicts RT-PCR analysis of total RNA obtained from rat myocardium pretreated with glucan (40 mg/Kg) for 1 hr. prior to 15 min. ischemia and 1 hr. reperfusion. TNFα and GAPDH are labeled at right to indicate the position of the corresponding RNA. M is a 100 bp DNA ladder. As indicated, pretreatment with glucan (I15'R1 hr+Glucan) decreases myocardial TNFα mRNA expression after I/R.
Figure 18:
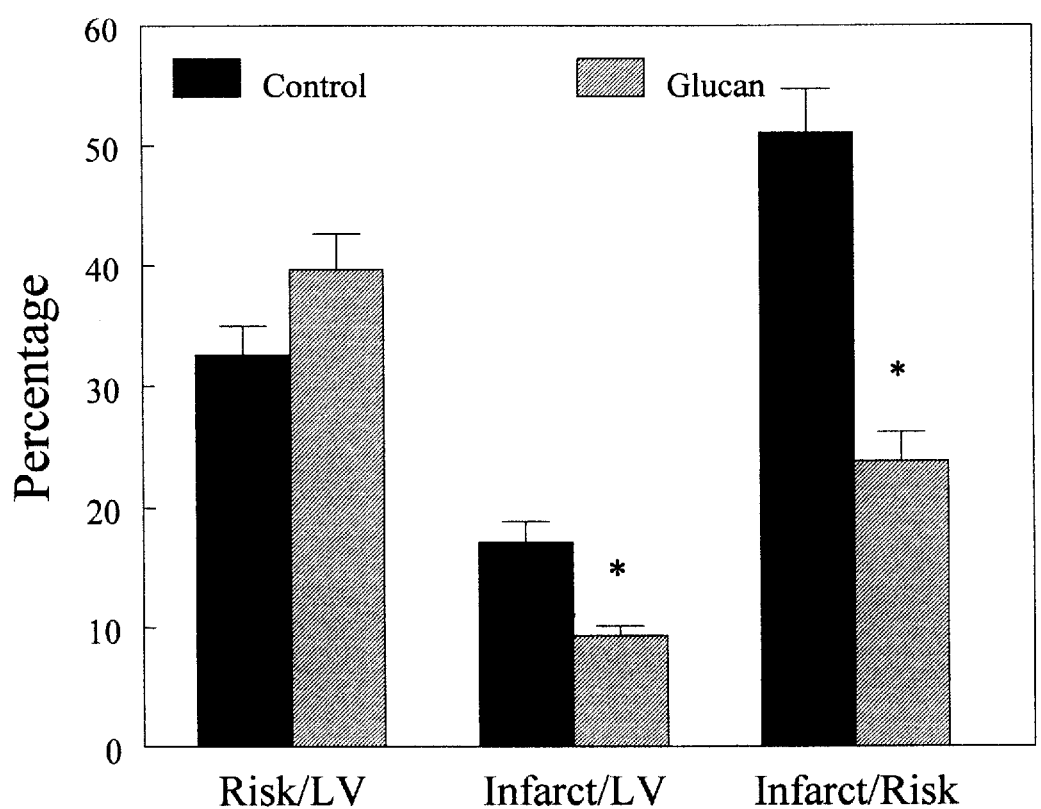
FIG. 18 is a graphic representation of results from TTC staining of post-ischemia tissue. Glucan phosphate (40 mg/kg) was administered intravenously 5 min. after onset of ischemia. Ischemia was then continued for an additional 40 min., followed by 4 hr. reperfusion. Infarct size was determined by TTC staining. Areas of left ventricle (LV), risk area (RA), and infarct area (IA) were scanned and quantified using an imaging analyzer. Values are expressed as means±SEM for 8–10 rats/group (P<0.05).

The inventors also investigated whether (1→3)-β-D-glucans regulate TNFα gene expression. As shown in FIG. 17, (1→3)-β-D-glucan significantly inhibited the expected I/R increase in TNFα mRNA levels. (1→3)-β-D-glucan down-regulates LPS-induced TNFα mRNA expression in vivo. In combination with the present data, this indicates that modulation of inflammatory cytokines is important for preventing myocardial I/R injury and that (1–3)-β-D-glucan treatment inhibits the inflammatory response while reducing myocardial I/R injury.

(1→3)-β-D-Glucan Markedly Reduced Cardiac Myocyte Apoptosis After J/R Injury The effects of (1→3)-β-D-glucan on apoptosis were investigated using rats treated with (1–3)-β-D-glucan (40 mg/kg) 1 hr. before the. hearts were subjected to 30 min. of ischemia followed by 3 hr. reperfusion. Upon completion of the protocol, the hearts were removed, rinsed free of blood, and perfused with freshly prepared phosphate-buffered 4% formaldehyde. Heart segments distal to the ligation were horizontally sliced into 2 mm sections and fixed with phosphate-buffered 4% formaldehyde at 4° C. overnight. The terminal deoxynucleotidyl transferase-mediated dUTP nick end-labeling (TUNEL) technique (Gavrieli, Y., et al., *J. Cell Biol.* (1992) 119: 493–501) was used to quantitate the level of apoptosis, using an In Situ Cell Death Detection Kit (Roche Diagnostics) and manufacturer's instructions. Briefly, three slides from each block were evaluated to determine the percentage of TUNEL positive cells. For each slide, four fields were randomly examined using a defined rectangular field area with magnification of 200×. A total of 100 cells were counted in each field. The TUNEL assay indicated a significant number of apoptotic cell nuclei (17.17±1.41%) in I/R hearts. In contrast, few apoptotic cell nuclei (3.33±0.71%) were found in (1→3)-β-D-glucan-treated I/R hearts indicating that I/R induced cardiac myocyte apoptosis is attenuated by (1→3)-β-D-glucan.

(1→3)-β-D-Glucan Administered Subsequent to Onset of Ischemia Also Reduces the Size of Both Infarct and Area at Risk Glucan phosphate (40 mg/kg) was administered to rats via intravenous route 5 min. after the rat hearts were subjected to occlusion of the left afterior descending (LAD) coronary artery, followed by 4 hr. reperfusion. Subsequently, the hearts were harvested and the infarct size/area at risk was determined using TTC staining and image analysis as described previously. FIG. 19 illustrates results, with infarct size expressed as percentage of risk area and risk area expressed as percentage of the left ventricle. As shown in FIG. 19, intravenous injection of glucan phosphate 5 min. after LAD occlusion significantly (p<0.05) reduced the infarce size/area at risk by 53% (24.39±2.00% v 51.03±3.69%) when compared to the control IR group, indicating that the level of protection obtained using (1→3)-β-D-glucan post-ischemia treatment is comparable to that obtained using (1→3)-β-D-glucan pre-ischemia treatment.

All publications are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. A method for reducing cardiac tissue ischemia/reperfusion damage in a mammalian subject having an acute ischemic condition or proximately under a condition associated with an imminent onset of ischemia, comprising administering to the subject a therapeutic dosage of about 1 mg to about 150 mg of a (1–3)-β-D-glucan per kilogram of the subject's body weight, wherein said (1–3)-β-D-glucan is selected from the group consisting of glucan sulphate, glucan phosphate, scleroglucan, or a combination thereof.

2. The method of claim 1 wherein the therapeutic dosage is about 25 mg/kg to about 125 mg/kg of the patient's body weight.

3. The method of claim 1 wherein the therapeutic dosage is administered prior to onset of ischemia.

4. The method of claim 1 wherein the therapeutic dosage is administered after onset of ischemia.

5. The method of claim 1 wherein the mammalian subject is a human.

6. The method of claim 1 wherein the therapeutic dosage is administered intravenously.

7. The method of claim 1 wherein the therapeutic dosage is administered orally.

8. The method of claim 1 wherein the therapeutic dosage is administered parenterally.

9. The method of claim 8 wherein the dosage is administered intraperitoneally.

10. A method for treating ischemia/reperfusion injury in a body organ of a mammalian subject having an acute ischemic condition or proximately under a condition associated with an imminent onset of ischemia in the organ, comprising administering to the subject a therapeutic dosage of about 1 mg to 150 mg of a (1–3)-β-D-glucan per kilogram of the subject's body weight, wherein said (1–3)-β-D-glucan is selected from the group consisting of glucan sulphate, glucan phosphate, scleroglucan, or a combination thereof.

11. The method of claim 10 wherein the therapeutic dosage is about 25 mg to 125 mg per kilogram of the subject's body weight.

12. The method of claim 10 wherein the body organ is a heart.

13. The method of claim 10 wherein the body organ is a lung.

14. The method of claim 10 wherein the body organ is a liver.

15. The method of claim 10 wherein the therapeutic dosage is administered prior to onset of ischemia/reperfusion injury.

16. The method of claim 10 wherein the therapeutic dosage is administered after onset of ischemia/reperfusion injury.

17. The method of claim 10 wherein the therapeutic dosage is administered intravenously.

18. The method of claim 10 wherein the therapeutic dosage is administered orally.

19. The method of claim 10 wherein the therapeutic dosage is administered parenterally.

20. The method of claim 10 wherein the ischemia/reperfusion injury results from a cardiovascular disease.

21. The method of claim 10 wherein the ischemia/reperfusion injury results from a traumatic injury.

22. A therapeutic method for decreasing ischemia/reperfusion damage in a mammalian subject having an acute ischemic condition caused by a spinal cord injury or proximately under a trauma from a spinal cord injury comprising administering to a subject a therapeutically effective dosage of (1→3)-β-D-glucan, wherein said (1–3)-β-D-glucan is selected from the group consisting of glucan sulphate, glucan phosphate, scleroglucan, or a combination thereof.

23. A therapeutic method for reducing ischemic injury to living tissue in a body limb of a mammalian subject proximately under an acute trauma associated with the onset of ischemia comprising systemically administering to a subject a therapeutically effective dosage of (1→3)-β-D-glucan, wherein said (1–3)-β-D-glucan is selected from the group consisting of glucan sulphate, glucan phosphate, scleroglucan, or a combination thereof.

24. The method of claim 23 wherein the therapeutically effective dosage is administered intravenously.

25. The method of claim 23 wherein the therapeutically effective dosage is administered by injection.

26. The method of claim 22 wherein the therapeutically effective dosage is administered orally.

* * * * *